United States Patent
Guha et al.

(10) Patent No.: US 9,463,189 B2
(45) Date of Patent: Oct. 11, 2016

(54) SULFONYL-SUBSTITUTED BICYCLIC COMPOUNDS AS PPAR MODULATORS FOR THE TREATMENT OF NON-ALCOHOLIC STEATOHEPATITIS

(71) Applicants: Mausumee Guha, San Diego, CA (US); Paul Grint, San Diego, CA (US)

(72) Inventors: Mausumee Guha, San Diego, CA (US); Paul Grint, San Diego, CA (US)

(73) Assignee: BPV Holdings, LLC, Solana Beach, CA (US)

( * ) Notice: Subject to any disclaimer, the term of this patent is extended or adjusted under 35 U.S.C. 154(b) by 198 days.

(21) Appl. No.: 13/894,143

(22) Filed: May 14, 2013

(65) Prior Publication Data

US 2013/0252970 A1    Sep. 26, 2013

Related U.S. Application Data

(63) Continuation of application No. 12/017,912, filed on Jan. 22, 2008, now abandoned.

(60) Provisional application No. 60/886,287, filed on Jan. 23, 2007.

(51) Int. Cl.
| | |
|---|---|
| *A61K 31/33* | (2006.01) |
| *A61K 31/495* | (2006.01) |
| *A61K 31/19* | (2006.01) |
| *A61K 31/4965* | (2006.01) |

(52) U.S. Cl.
CPC ............. *A61K 31/495* (2013.01); *A61K 31/19* (2013.01); *A61K 31/4965* (2013.01)

(58) Field of Classification Search
None
See application file for complete search history.

(56) References Cited

U.S. PATENT DOCUMENTS

| | | | |
|---|---|---|---|
| 4,237,130 A | 12/1980 | Cragoe, Jr. et al. | |
| 4,600,709 A | 7/1986 | Ballenegger et al. | |
| 5,464,788 A | 11/1995 | Bock et al. | |
| 5,756,504 A | 5/1998 | Bock et al. | |
| 6,465,468 B1 | 10/2002 | Baxter et al. | |
| 6,673,799 B1 | 1/2004 | Taniguchi et al. | |
| 6,852,718 B2 | 2/2005 | Burkamp et al. | |
| 6,939,875 B2 | 9/2005 | Auerbach et al. | |
| 7,494,999 B2 | 2/2009 | Noble et al. | |
| 7,517,884 B2 | 4/2009 | Malecha et al. | |
| 7,834,004 B2 | 11/2010 | Noble et al. | |
| 2004/0180925 A1 | 9/2004 | Matsuno et al. | |
| 2004/0224957 A1 | 11/2004 | Sharma et al. | |
| 2005/0070532 A1 | 3/2005 | Liu et al. | |
| 2005/0107445 A1 | 5/2005 | Watkins et al. | |
| 2005/0124625 A1 | 6/2005 | Salvati et al. | |
| 2005/0153981 A1 | 7/2005 | Li et al. | |
| 2005/0203151 A1 | 9/2005 | Malecha et al. | |
| 2005/0234046 A1 | 10/2005 | Zhao et al. | |
| 2006/0167012 A1 | 7/2006 | Noble et al. | |
| 2006/0199820 A1 | 9/2006 | Bannen et al. | |
| 2006/0205735 A1 | 9/2006 | Glardina et al. | |
| 2006/0205736 A1 | 9/2006 | Noble et al. | |
| 2006/0258683 A1 | 11/2006 | Liu et al. | |
| 2007/0093504 A1 | 4/2007 | Bennett et al. | |
| 2007/0190079 A1 | 8/2007 | Shiau et al. | |
| 2007/0208026 A1 | 9/2007 | Liu et al. | |
| 2007/0219193 A1 | 9/2007 | Zhao | |
| 2007/0249519 A1 | 10/2007 | Guha | |
| 2007/0270432 A1 | 11/2007 | Gallagher et al. | |
| 2008/0004281 A1 | 1/2008 | Rao et al. | |
| 2008/0176861 A1 | 7/2008 | Guha et al. | |
| 2008/0287477 A1 | 11/2008 | Malecha et al. | |
| 2009/0029971 A1 | 1/2009 | Noble et al. | |
| 2009/0143396 A1 | 6/2009 | Malecha et al. | |
| 2009/0227599 A1 | 9/2009 | Noble et al. | |
| 2009/0264417 A1 | 10/2009 | Noble et al. | |

FOREIGN PATENT DOCUMENTS

| | | |
|---|---|---|
| CA | 1095923 A1 | 2/1981 |
| EP | 0107622 A1 | 5/1984 |
| EP | 0158596 A2 | 10/1985 |
| EP | 548798 A1 | 6/1993 |
| EP | 0173899 A2 | 3/1996 |
| EP | 1236719 A1 | 9/2002 |
| JP | 2001261657 A | 9/2001 |
| WO | 9525443 A1 | 9/1995 |
| WO | 9725042 A1 | 7/1997 |
| WO | 9857949 A1 | 12/1998 |
| WO | 9937304 A1 | 7/1999 |
| WO | 0012074 A2 | 3/2000 |
| WO | 0056704 A1 | 9/2000 |
| WO | 0107622 A2 | 2/2001 |
| WO | 0158596 A1 | 8/2001 |
| WO | 0174797 A1 | 10/2001 |
| WO | 0226729 A2 | 4/2002 |
| WO | 02051836 A1 | 7/2002 |
| WO | 02100822 A1 | 12/2002 |
| WO | 03082288 A1 | 10/2003 |
| WO | 2004/005253 A1 | 1/2004 |
| WO | 2004060871 A1 | 7/2004 |
| WO | 2004073606 A2 | 9/2004 |
| WO | 2004092117 A1 | 10/2004 |

(Continued)

OTHER PUBLICATIONS

Moller et al (Int J Obesity 27:S17-S21, 2003).*

(Continued)

*Primary Examiner* — Craig Ricci

(74) *Attorney, Agent, or Firm* — Dennis A. Bennett; Cynthia Hathaway

(57) ABSTRACT

Disclosed herein are new methods of treatment of non-alcoholic fatty liver disease (NAFLD), non-alcoholic steatohepatitis (NASH), and other fibrotic diseases of the liver in a subject by modulating PPARδ with sulfonyl-substituted bicyclic compounds and compositions as pharmaceuticals.

2 Claims, 6 Drawing Sheets

(56) References Cited

FOREIGN PATENT DOCUMENTS

| WO | 2004092130 A2 | 10/2004 |
|---|---|---|
| WO | 2004093879 A1 | 11/2004 |
| WO | 2005011653 A2 | 2/2005 |
| WO | 2005011654 A2 | 2/2005 |
| WO | 2005011656 A2 | 2/2005 |
| WO | 2005011657 A2 | 2/2005 |
| WO | 2005016881 A1 | 2/2005 |
| WO | 2005040136 A1 | 5/2005 |
| WO | 2005044797 A1 | 5/2005 |
| WO | 2005060958 A1 | 7/2005 |
| WO | 2006014168 A1 | 2/2006 |
| WO | 2006034297 A1 | 3/2006 |
| WO | 2006034315 A2 | 3/2006 |
| WO | 2006034338 A1 | 3/2006 |
| WO | 2006034341 A2 | 3/2006 |
| WO | 2006034410 A2 | 3/2006 |
| WO | 2006034440 A2 | 3/2006 |
| WO | 2006034441 A1 | 3/2006 |
| WO | 2006034446 A2 | 3/2006 |
| WO | 2006343212 A1 | 3/2006 |
| WO | 2006055187 A1 | 5/2006 |
| WO | 2008043024 A2 | 4/2008 |

OTHER PUBLICATIONS

Bedu et al., "Peroxisome Proliferator-Activated Receptor Beta/Delta as a Therapeutic Target for Metabolic Diseases," Expert Opin. Thera. Targets, 9(4), 2005, pp. 861-873.

Calamita et al., "Present and Future Therapeutic Strategies in Non-Alcoholic Fatty Liver Disease," Expert Opin. Thera. Targets, 11(9), 2007, pp. 1231-1249.

Falck-Ytter et al., "Clinical Features and Natural History of Nonalcoholic Steatosis Syndromes," Seminars in Liver Disease, 2001, 21:1, pp. 17-26.

Fromenty et al., "The Ins and Outs of Mitchondrial Dysfunction in NASH," Diabetes & Metabolism, Apr. 2004, vol. 30, Issue 2, pp. 121-138.

Hellemans etal., "Peroxisome Proliferator-Activated Receptor-Beta Signaling Contributes to Enhanced Proliferation of Hepatic Stellate Cells," Gastroenterology, 2003, 124, pp. 184-201.

Iwaisako et al., Protection from Liver Fibrosis by a Peroxisome Proliferator-Activated Receptor δ Agonist; Department of Medicine and Radiology, University of California at San Diego, LaJolla, CA 92093 PNAS Early Edition.

Kanda et al., "MCP-1 Contributes to Macrophage Infiltration into Adipose Tissue, Insulin Resistance, Hepatic Steatosis in Obesity,", J. Clin. Invest., 2006, 116, pp. 1494-1505.

Nagasawa et al., "Effects of Bezafibrate, PPAR Pan-Agonist and GW501516, PPAR Agonist on Development of Steatohepatitis in Mice Fed a Methionine- and Choline-Deficient Diet," European Journal of Pharmacology, 536, 2006, pp. 182-191.

Neuschwander-Tetri et al, Hepatology 38:1008-1017, 2003.

Reddy et al., "Nonalcoholic Steatosis and Steatohepatitis III Peroxisomal b-Oxidation, PPARa and Steatohepatitis," Am J Physiol Gastrointest Liver Physiol, G1333-G1339, 2001.

Sanyal et al., "Nonalcoholic Steatohepatitis: Association of Insulin Resistance and Mitochondrial Abnormalities," Gastroenterology, 120, 2001, pp. 1183-1192.

Stella et al., Prodrugs: Challenges and Rewards, Part 1, 2007.

Vigano et al., "Insulin Resistance Influences Iron Metabolism and Hepatic Steatosis in Type II Diabetes," Gastroenterology, 118, 2000, pp. 986-987.

\* cited by examiner

SULFONYL-SUBSTITUTED BICYCLIC COMPOUNDS AS PPAR MODULATORS FOR THE TREATMENT OF NON-ALCOHOLIC STEATOHEPATITIS This application is a continuation of U.S. application Ser. No. 12/017,912, filed Jan. 2, 2008, which claims the benefit of priority of U.S. provisional application No. 60/886,287, filed Jan. 23, 2007, the disclosures of which are hereby incorporated by reference as if written herein in their entireties.

Disclosed herein are new methods of treatment of non-alcoholic fatty liver disease (NAFLD), non-alcoholic steatohepatitis (NASH), and other fibrotic diseases of the liver in a subject by modulating PPARδ with sulfonyl-substituted bicyclic compounds and compositions as pharmaceuticals.

Nonalcoholic steatohepatitis or NASH is a liver disease which resembles alcoholic hepatitis on liver biopsy, but occurs in patients who have no known history of alcohol abuse. First described by Luwig et al., (Ludwig, J. *Mayo Clin Proc.* (1980) 55:434-438), NASH is characterized by hyperinsulinemia, insulin resistance, hyperlipidemia, elevated serum transaminases such as aspartate aminotransferase (AST) and alanine aminotransferase (ALT) and liver cell injury driven by lipid accumulation, hepatic inflammation and lobular infiltration of inflammatory cells such as macrophages, and activation and transformation of hepatic stellate cells into smooth muscle cell phenotype. In humans, NAFLD progresses from the relatively benign stage of hepatic steatosis through an intermediary stage of NASH in which fibrosis appears and begins to accumulate, to frank cirrhosis culminating in liver failure. There is no single cause of NASH, which is diagnosable only with a liver biopsy. Liver function tests determine blood levels of substances produced or metabolized by the liver and are helpful to diagnosing NASH and differentiating it from alcoholic hepatitis, but are not dispositive. While not every person with NASH develops cirrhosis, once serious scarring or cirrhosis is present, few treatments are currently available that can inhibit or halt the progression. Liver transplantation is the only direct treatment for advanced cirrhosis with liver failure, and transplantation is increasingly performed in people with NASH. Ironically, the disease takes a double toll on public health in this regard, since the increasing prevalence of NAFLD and NASH has reduced the available pool of liver donors for other diseases—not only because there are more NASH patients in need, but also because even mild hepatic fibrosis can make a liver unsuitable for transplant into would-be recipients. NASH ranks as one of the major causes of cirrhosis in America, behind hepatitis C and alcoholic liver disease.

NASH is frequently associated with another frequent and harmful condition, the metabolic syndrome (see *Circulation* (2002) 106:3143-3421 for the National Cholesterol Education Program (NCEP) consensus criteria for metabolic syndrome, and Dandona, P et al. Circulation. 2005 Mar. 22; 111(11):1448-54, for a review of the metabolic syndrome as an interaction between diabetes, inflammation, and obesity). NASH frequently occurs in persons with conditions related to the metabolic syndrome such as obesity, diabetes mellitus, hyperlipidemia, high LDL cholesterol, low HDL cholesterol, and insulin resistance, to name but a few. The link between the metabolic syndrome and NAFLD can be partly explained by insulin resistance (Vigano M et al., *Gastroenterology* (2000) 118:986-987, Sanyal A J, *Gastroenterology* (2001) 120:1183-1192), excessive accumulation of triglycerides within hepatocytes in the absence of significant alcohol ingestion (Falck-Ytter Y et al., *Semin. Liver Dis.* (2001) 21:17-26) and cytokine production. A more complete review of the NASH-metabolic syndrome link is beyond the scope of this disclosure, and at any rate would simply recapitulate what is well known in the art.

Insulin resistance is associated with fat accumulation in the liver, a condition termed nonalcoholic fatty liver disease (NAFLD). Excess fat in the liver is not necessarily a benign condition. Some patients with NAFLD develop necroinflammatory response which is characteristic of NASH and a fraction of those will develop cirrhosis. As many as 20% all adults have NAFLD and 2% to 3% of adults may be afflicted with NASH. Of these, approximately 20% of patients with NASH are at risk for developing cirrhosis and subsequently dying from end-stage liver diseases (Neuschwander et al. *Am. J. Med. Sci.* 2005, 330(6):326-35.) such as hepatocellular carcinoma. The loss of insulin inhibitory effect triggers upregulation mechanisms with activation of peroxisomal β-oxidation (Robertson G et al., *Am. J. Physiol Gastrointest. Liver Physiol.* (2001) 281:G1 135-G1 139) and intracellular oxidative stress (Choi S and Diehl A M, *Curr. Opin. Gastroenterol.* (2005) 21:702-707). This and other research indicates that defective states of peroxisomal β-oxidation pathway may play an important role in the development of steatohepatitis (Reddy J K: *Am. J. Physiol Gastrointest. Liver Physiol.* (2001) 281:G1333-G1339).

Peroxisome proliferators are a structurally diverse group of compounds which, when administered to mammals, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, *Ann. Rev. Cell Biol.* 1:489-530 (1985); Vamecq and Draye, *Essays Biochem.* 24:1115-225 (1989); and Nelali et al., *Cancer Res.* 48:5316-5324 (1988)). Insight into the mechanism whereby peroxisome proliferators exert their pleiotropic effects was provided by the identification of a member of the nuclear hormone receptor superfamily activated by these chemicals (Isseman and Green, Nature 347-645-650 (1990)), termed peroxisome proliferator activated receptors (PPARs). Subtypes include PPAR-alpha and the later-discovered PPAR-delta (also known as NUC1, PPAR-beta and FAAR) and two isoforms of PPAR-gamma. These PPARs can regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endoodn. Met.* 291-296, 4 (1993)).

Biological processes well-known to be modulated by PPARs include, for example, plasma lipid transport and fatty acid catabolism, regulation of insulin sensitivity and blood glucose levels, which are involved in hypoglycemia/hyperinsulinemia (resulting from, for example, abnormal pancreatic beta cell function, insulin secreting tumors and/or autoimmune hypoglycemia due to autoantibodies to insulin, the insulin receptor, or autoantibodies that are stimulatory to pancreatic beta cells), macrophage differentiation which lead to the formation of atherosclerotic plaques, inflammatory response, carcinogenesis, hyperplasia, and adipocyte differentiation.

Due to its role as a regulator of fatty acid catabolism and energy homeostasis, PPAR-delta (or alternatively, PPARδ, PPARβ, or NUC1) has emerged as an attractive target for the treatment of diseases associated with the metabolic syndrome (Bedu E et al., *Expert Opin Ther. Targets*, (2006) 9(4):861-874). For example, in a recent study in insulin-resistant obese rhesus monkeys, a potent and selective PPARδ compound was shown to decrease VLDL and increase HDL in a dose response manner (Oliver et al., *Proc. Natl. Acad. Sci. USA*. 98: 5305, 2001).

Selective activation of PPARδ provides a therapeutic approach to the treatment of NASH, for which there are currently no specifically identified therapies (Calamita, G. and Portincasa, P. *Expert Opin Ther Targets*. 2007 September; 11(9):1231-49). Instead, current treatments are directed towards rectifying some of the attendant disorders, such as obesity, diabetes and hyperlipidemia, either with appropriate pharmacotherapy or behavior modification. Antidiabetic medications such as metformin, rosiglitazone, and pioglitazone are currently being studied in patients with NASH in an effort to improve insulin sensitization. Certain experimental approaches under evaluation include the use of antioxidants, such as vitamin E, selenium, and betaine, which act by reducing the hepatic oxidative stress associated with NASH. The drug rimonabant, a CB1 receptor inverse agonist which is approved for use as an anti-obesity agent ex-United States but which was withdrawn from the FDA approval process due to safety concerns (Sanofi-Aventis press release, Jun. 13, 2007 via PRNewswire-FirstCall), has shown positive outcome in a less stringent genetically obese rodent model (Gary-Bobo, M. et al., *Hepatology* 2007 July; 46(1):122-9).

Recently, in a methionine- and choline-deficient diet model of NASH, PPARδ agonist GW501516 (GlaxoSmithKline) improved hepatic steatosis and ameliorated fatty acid β-oxidation, showing a direct prevention of inflammation. This effect was associated with increased fatty acid β-oxidation and decreased hepatic triglyceride deposition, inflammation, number of activated hepatic stellate cells and inflammatory cytokines or chemokines (Nagasawa T et al., *Eur. J. Pharmacol*. (2006) 536:182-191). Development on this compound has been widely reported to have been discontinued, however, possibly due to side effects having to do with off-target cross reactivity. Clearly, a need still exists to discover and develop PPARδ activators for the treatment of NASH which avoid toxicological liabilities.

The present disclosure provides for methods of treating NASH and NASH-related disorders and conditions by administering a therapeutically effective amount of a modulator of peroxisome proliferator-activated receptor ("PPAR") to a subject in need thereof. Specifically, the provided herein are methods of treatment of NASH comprising administrating a therapeutically effective amount of a compound defined by the structural Formula (I):

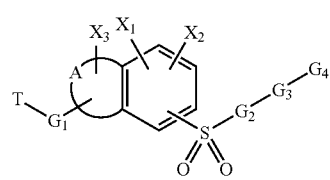

(I)

Or a salt, ester, or prodrug thereof, wherein;

A is a saturated or unsaturated hydrocarbon chain or a heteroatom-comprising hydrocarbon chain having from 3 to 5 atoms, forming a five- to seven-membered ring;

T is selected from the group consisting of —C(O)OH, —C(O)NH$_2$, and tetrazole;

$G_1$ is selected from the group consisting of —(CR$^1$R$^2$)$_n$—, —Z(CR$^1$R$^2$)$_n$—, —(CR$^1$R$^2$)$_n$Z—, —(CR$^1$R$^2$)$_r$Z(CR$^1$R$^2$)$_s$—;

Z is O, S or NR;

n is 0, 1, or 2;

r and s are independently 0 or 1;

R$^1$ and R$^2$ are independently selected from the group consisting of hydrogen, halo, optionally substituted lower alkyl, optionally substituted lower heteroalkyl, optionally substituted lower alkoxy, and lower perhaloalkyl or together may form an optionally substituted cycloalkyl;

$X_1$, $X_2$, and $X_3$ are independently selected from the group consisting of hydrogen, optionally substituted lower alkyl, optionally substituted cycloalkyl, halogen, perhaloalkyl, hydroxy, optionally substituted lower alkoxy, nitro, cyano, and NH$_2$;

$G_2$ is selected from the group consisting of a saturated or unsaturated cycloalkyl or heterocycloalkyl linker, optionally substituted with $X_4$ and $X_5$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, NH$_2$, and CO$_2$R;

R is selected from the group consisting of optionally substituted lower alkyl and hydrogen;

$G_3$ is selected from the group consisting of a bond, a double bond, —(CR$^3$R$^4$)$_m$—, carbonyl, and —(CR$^3$R$^4$)$_m$CR$^3$=CR$^4$—;

m is 0, 1, or 2;

R$^3$ and R$^4$ are independently selected from the group consisting of hydrogen, optionally substituted lower alkyl, optionally substituted lower alkoxy, optionally substituted aryl, lower perhaloalkyl, cyano, and nitro;

$G_4$ is selected from the group consisting of hydrogen, optionally substituted aryl, optionally substituted heteroaryl, optionally substituted cycloalkyl, optionally substituted cycloheteroalkyl, optionally substituted cycloheteroaryl, optionally substituted cycloalkenyl, and —N=(CR$^5$R$^6$); and R$^5$ and R$^6$ are independently selected from the group consisting of hydrogen, optionally substituted aryl, optionally substituted heteroaryl, optionally substituted cycloalkyl, optionally substituted cycloalkenyl, and optionally substituted cycloheteroalkyl.

The sulfonyl-substituted bicyclic compounds described herein modulate at least one peroxisome proliferator-activated receptor (also referred to as "peroxisome proliferator") function by contacting the PPAR with a compound of Formula I, as described herein. The PPAR may be PPARα, PPARδ, and PPARγ. Compounds described herein may be modulating both PPARδ and PPARγ or PPARα and PPARδ, or all three PPAR subtypes, or selectively modulating predominantly PPARγ, PPARα or PPARδ. In certain embodiments, the modulation is selective for PPARδ over PPARα and PPARγ, and such selectivity is greater than 100-fold over other isoforms. In further embodiments, the modulation is 200- to 500-fold selective over said other isoforms.

Pharmaceutical compositions comprising the compounds of the Formula I together with a pharmaceutically acceptable diluent or carrier may also be used in connection with the methods of the provided herein.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein:

FIG. 1C1 as compared to 1C2 shows increased size of adipocytes in NASH vs. normal mice, indicative of visceral adiposity. FIG. 1C3 as compared to 1C4 shows increased deposition of liver fatty tissue (LFT) as visualized with Oil Red O stain in NASH vs. normal mice, indicative of hepatic steatosis. FIG. 1C5 as compared to 106 shows increased fibrosis and altered cellular morphology in liver tissue as visualized with trichrome stain in NASH vs. normal mice, indicative of hepatic fibrosis.

FIG. 5 is a comparison of the percent weight loss (from day 1 vs. the last day of the study) as between six groups: NC-fed mice receiving either the compound of Example 2 (Compound 2, 42 days of 10 mg/kg/day) or vehicle, HFD-fed mice receiving either the compound of Example 2 (Compound 2, 42 days of 5 mg/kg/day) or vehicle, and HFD-fed mice receiving either the compound of Example 2 (Compound 2, 42 days of 10 mg/kg/day) or vehicle.

Figure 1A:
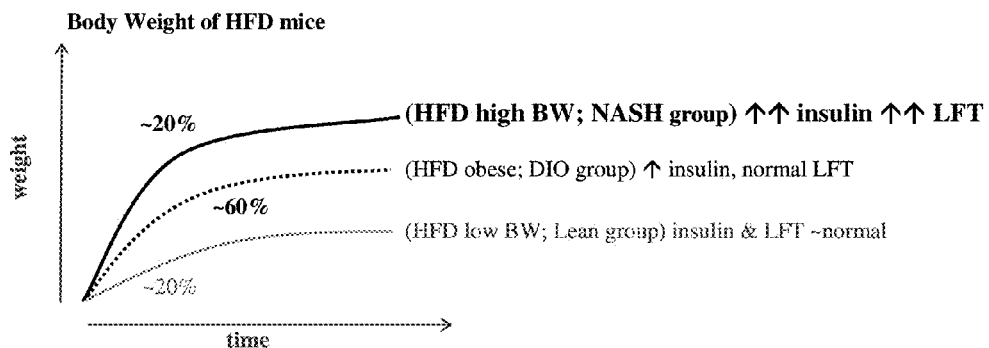
FIG. 1A is a visual representation of the first phase of the preclinical murine model of nonalcoholic steatohepatitis (NASH) discussed in Example 4, depicting the effect of a high fat diet (HFD) on body weight, insulin, and liver fatty tissue (LFT) of mice. Approximately 20% of mice on a HFD will develop a phenotype featuring a very high body weight, as well as markedly elevated insulin and LFT, dubbed the HFH (high-fat diet, high body weight) or NASH group; another 60% of mice on a HFD will develop a phenotype featuring an elevated body weight and insulin and normal LFT, dubbed the DIO (diet-induced obesity) group; and 20% of mice on a HFD will develop a phenotype featuring a normal insulin and LFT levels, dubbed the HFL (high-fat diet, low body weight) group. It is provided as a visual aid only and is not quantitative.
Figure 1B:
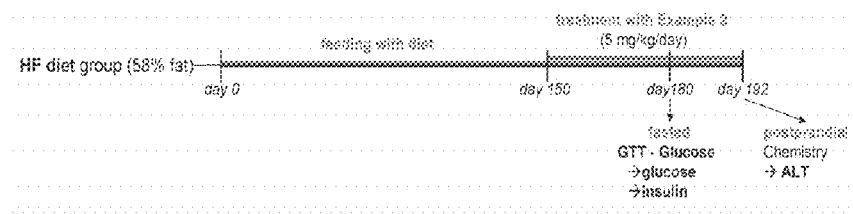
FIG. 1B provides a timeline for the preclinical model of FIG. 1A, in which mice are HFD-fed for 120-150 days before start of treatment with compound.

The following abbreviations are used herein:
ALT alanine aminotransferase
AST aspartate aminotransferase
BSA bovine serum albumin
Cas # chemical abstracts service number
Cat # catalogue number
DAPI diamidinophenylindole
DIO diet induced obesity
EDTA ethylenediaminetetraacetic acid
EDTA ethylenediaminetetraacetic acid
ELISA enzyme-linked immunoabsorbent assay
FFPE formalin fixed paraffin embedded
FITC fluorescein isothiocyanate
HDL high density lipoprotein
HFD high fat diet
HFH high fat diet, high body weight group
HFL high fat diet, low body weight group
LL lower limit
LOQ limit of quantification
NC normal chow fed group
NDC national drug code
O.C.T. optimal cutting temperature
PBS phosphate buffered saline
RNA ribonucleic acid
UL upper limit
U/L Units per liter Provided herein are methods of treating liver diseases including NAFLD, NASH and cirrhosis in a subject in need thereof by administering to the subject a therapeutic amount of a PPARδ agonist compound so as to slow or stop the progression of NASH and related hepatic fibrosis.

In certain embodiments, the PPARδ agonist is a compound of Formula I. Compounds that are selective activators of PPARδ include those where T is —C(O)OH. In other embodiments, in compounds of Formula I, group A has three atoms and forms a five-membered ring. In related embodiments, at least one of said three atoms of A is a heteroatom selected from the group consisting of N, O, and S.

In certain embodiments, compounds of Formula I may have the structural formula selected from the group consisting of:

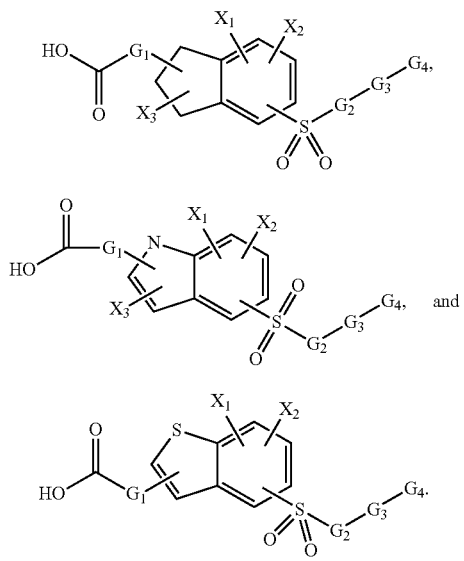

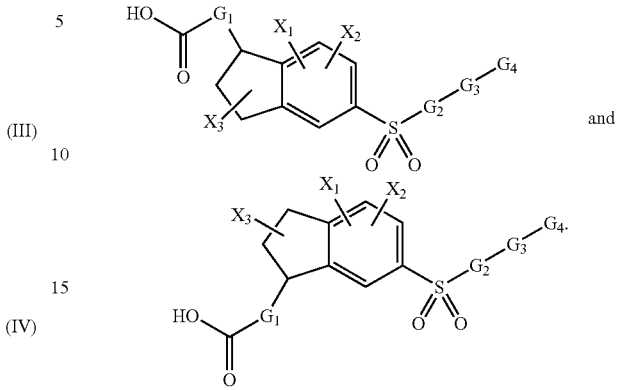

Compounds of Formula I may also have a structural formula selected from the group consisting of:

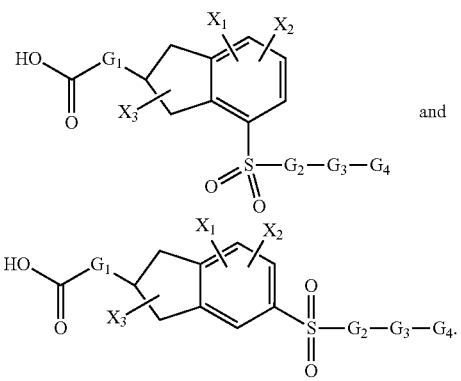

In other embodiments, compounds of Formula I have a structural formula selected from the group consisting of:

Compounds of Formula I may also have a structural formula (III) selected from the group consisting of:

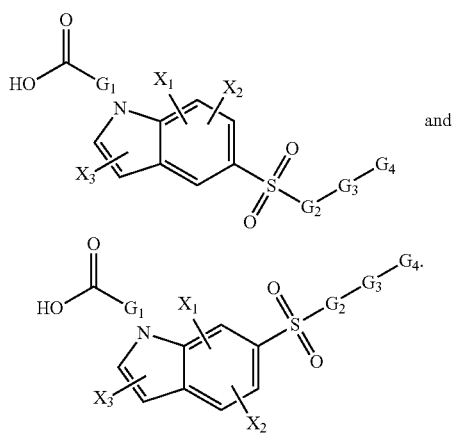

Compounds of Formula I may also have a structural formula (IV) selected from the group consisting of:

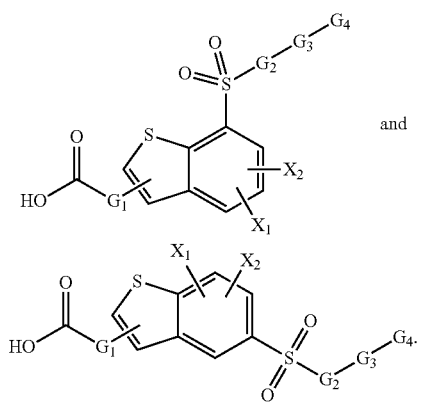

In certain embodiments, compounds of Formula I include groups wherein:
$G_1$ is —$(CR^1R^2)_n$—;
With the proviso that if A is a 5 carbon chain, n is 0 or 1;
$G_2$ has the structure:

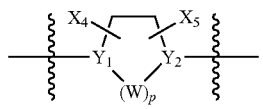

$Y_1$ and $Y_2$ are independently selected from the group consisting of N and C—$X_6$;
$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$, or $X_4$ and $X_5$ together may form a cycloalkyl;
R is selected from the group consisting of lower alkyl and hydrogen;
p is 1, 2 or 3;
W is selected from the group consisting of —$CX_4X_5$— and N—$X_7$;
$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$;

$X_6$ is selected from the group consisting of hydrogen, alkyl, hydroxy, alkoxy, cyano, halogen, lower perhaloalkyl and $NH_2$ or null when forming a double bond with an adjacent ring atom; and $X_7$ is selected from the group consisting of hydrogen, alkyl, hydroxy, and lower perhaloalkyl, or null when forming a double bond with $Y_2$.

Compounds Formula I also include compounds wherein p is 2, W is —$CX_4X_5$—, and $Y_1$ is N. In other embodiments, p is 2, W is —$CX_4X_5$—, and $Y_1$ and $Y_2$ are N.

Compounds of Formula I further include compounds wherein $G_1$ is —$(CR^1R^2)_n$—. In certain embodiments, n is 0 or 1. In other embodiments, $R^1$ and $R^2$ may be independently selected from the group consisting of hydrogen, methyl, ethyl, and propyl, or together may form a cyclopropyl, cyclobutyl, cyclopentyl, or cyclohexyl. In further embodiments, $R^1$ and $R^2$ are hydrogen.

Compounds of Formula I include compounds wherein $G_3$ is a bond. In other embodiments, $G_3$ is lower alkylene. In further embodiments, $G_3$ is methylene.

In certain embodiments, compounds of Formula I include compounds wherein $G_4$ is selected from the group consisting of optionally substituted aryl and optionally substituted heteroaryl. In certain embodiments, $G_4$ may be optionally substituted phenyl or optionally substituted pyridinyl. In further embodiments, $G_4$ may be singly or doubly substituted with halogen, lower alkyl, lower perhaloalkyl, lower haloalkoxy, or lower perhaloalkoxy. In related embodiments, $G_4$ may have a structural formula selected from the group consisting of:

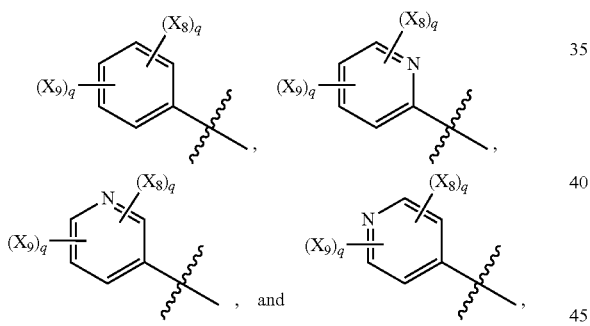

wherein:

q is 1 to 3;

$X_8$ and $X_9$ are independently selected from the group consisting of hydrogen, alkyl, halogen, lower perhaloalkyl, lower perhaloalkoxy or mono- or di-haloalkoxy, hydroxy, alkoxy, nitro, cyano, $NH_2$, and $CO_2R$; and R is selected from the group consisting of lower alkyl and hydrogen.

Further, compounds of Formula I may have the structural formulae selected from the group consisting of:

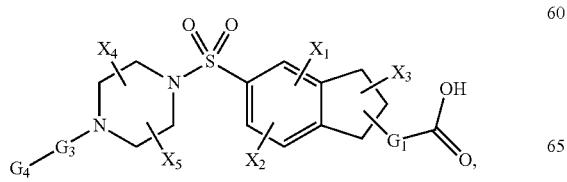

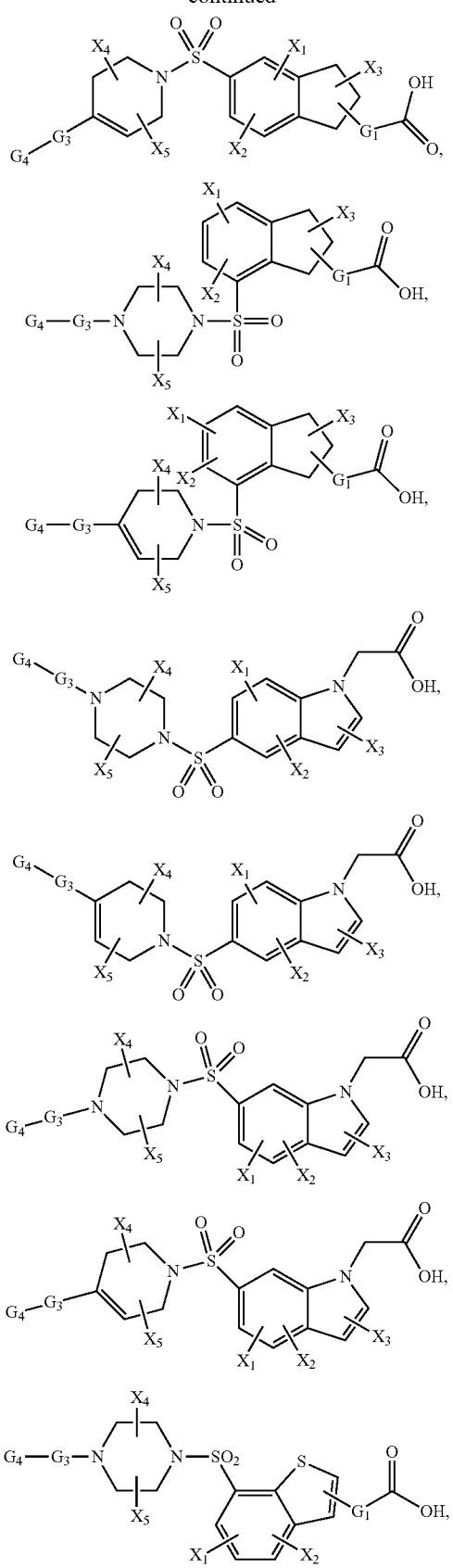

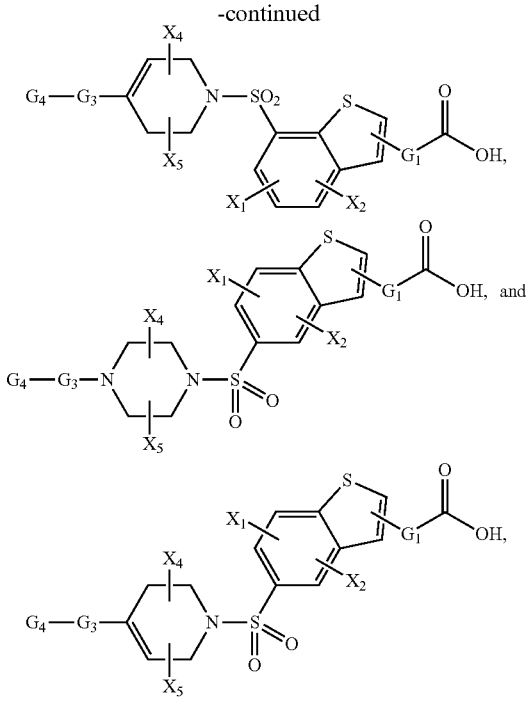

wherein G$_1$ is selected from the group consisting of —(CR$^1$R$^2$)$_n$— and —(CR$^1$R$^2$)$_n$O—, and other groups are as previously defined.

Compounds of Formula I include compounds wherein X$_1$, X$_2$, and X$_3$ are independently selected from the group consisting of hydrogen, halogen, lower alkyl, and lower alkoxy. In further embodiments, X$_1$, X$_2$, and X$_3$ are independently selected from the group consisting of hydrogen, methyl, ethyl, propyl, and halogen. In yet further embodiments, X$_1$, X$_2$, and X$_3$ may be independently selected from the group consisting of hydrogen and methyl.

Another aspect of the methodologies provided herein includes the administration of pharmaceutical compositions comprising compounds of Formula I together with pharmaceutically acceptable diluents or carriers.

Compounds of Formula I, disclosed herein, can modulate at least one peroxisome proliferator-activated receptor (PPAR) function. Compounds described herein may be activating both PPARδ and PPARγ or PPARα and PPARδ, or all three PPAR subtypes, or selectively activating predominantly PPARγ, PPARα or PPARδ. In certain embodiments, PPARδ is selectively modulated.

Thus, the methods of treating liver diseases such as NAFLD and NASH include modulating at least one peroxisome proliferator-activated receptor (PPAR) function comprising the step of contacting the PPAR with a compound of Formula I, as described herein. The change in cell phenotype, cell proliferation, activity of the PPAR, expression of the PPAR or binding of the PPAR with a natural binding partner may be monitored. Such methods may be modes of treatment of disease, biological assays, cellular assays, biochemical assays, or the like.

In another aspect, the subject methods of treatment comprise identifying a patient in need, administering a therapeutically effective amount of a compound of Formula I or a pharmaceutically acceptable salt, ester, amide, or prodrug thereof. Provided herein are methods of treating liver diseases such as NAFLD and NASH comprising the administration of a therapeutic amount of a compound of Formula I. The PPAR may be selected from the group consisting of PPARα, PPARδ, and PPARγ. In certain embodiments, the PPAR is PPARδ.

In certain embodiments, the liver disease to be treated by the administration of a compound or salt thereof is a metabolic liver disease.

In certain embodiments, said liver disease is also a fibrotic liver disease.

In certain embodiments, said liver disease is selected from the group consisting of NAFLD, NASH, and cirrhosis.

Also provided herein is a method of preventing or reducing hepatic fibrosis comprising the administration of a compound selected from the group consisting of Compounds 1 and 2, or a salt thereof.

Also provided herein is a method of preparing a liver for surgery comprising the administration of a compound selected from the group consisting of Compounds 1 and 2, or a salt thereof prior to surgery.

In certain embodiments, said surgery is liver transplant surgery.

In certain embodiments, said compound is (S)-4-[cis-2,6-dimethyl-4-(4-trifluoromethoxy-benzyl)-piperazine-1-sulfonyl]-indan-2-carboxylic acid tosylate.

In certain embodiments, said administration achieves the effect of reducing fibrosis in said liver.

As used herein, the terms below have the meanings indicated.

When ranges of values are disclosed, and the notation "from n$_1$ . . . to n$_2$" is used, where n$_1$ and n$_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4- butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—$NR_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that, where no particular stereochemical isomer is indicated, the compounds to be used in the methods provided herein may encompass all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. Thus, unless otherwise specifically indicated, the compounds to be used in the methods provided herein include all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms. Where a particular stereochemical, geometric, tautomeric, or other isomer is indicated, such an isomer is presumed to be isolated to a substantial degree. Degrees of "isolation" "to a substantial degree" include isolation to greater than or equal to 70%, 80%, 85% 90%, 95%, 97%, 98%, 99%, or more.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

In the event that $G_3$ is designated to be "a bond", the structure shown below (right side) is intended: the entity designated $G_3$ collapses to a single bond connecting $G_2$ and $G_4$:

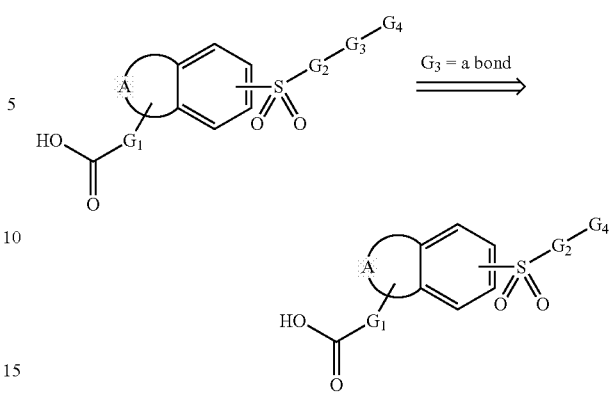

Similarly, when, within $G_1$, n is 0 or both r and s are 0, $G_1$ collapses to a bond connecting A and T.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "NASH" means non-alcoholic steatohepatitis. However, NASH falls along a continuum of liver diseases associated with symptoms of the metabolic syndrome and characterized by increasing fibrosis, including NAFLD, hepatic steatosis, NASH, and cirrhosis. In this context, it is intended that methods applicable to NASH will also be applicable to other liver diseases.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "modulate" refers to the ability of a compound of the provided herein to alter the function of a PPAR. A modulator may activate a PPAR. The term "modulate" also refers to altering the function of a PPAR by increasing or decreasing the probability that a complex forms between a PPAR and a natural binding partner. A modulator may increase the probability that such a complex forms between the PPAR and the natural binding partner, may increase or decrease the probability that a complex forms between the PPAR and the natural binding partner depending on the concentration of the compound exposed to the PPAR, and or may decrease the probability that a complex forms between the PPAR and the natural binding partner.

The term "activate" refers to increasing the cellular function of a receptor, in this case PPARδ. An "activator," or "agonist," compound is one capable of combining with a specific receptor (PPARδ) and initiating the same reaction or activity typically produced by its natural ligand. The term "agonist" includes full and partial agonists, and co-agonists.

"PPAR modulator" is used herein to refer to a compound that exhibits an $EC_{50}$ with respect to PPAR activity of no more than about 100 μM and more typically not more than about 50 μM, as measured in the PPAR in vitro assay described generally hereinbelow. "$EC_{50}$" is that concentration of modulator which either activates or reduces the activity of an enzyme (e.g., PPAR) to half-maximal level. Certain compounds disclosed herein have been discovered to exhibit modulatory activity against PPAR. In certain embodiments, compounds will exhibit an $EC_{50}$ with respect to PPAR of no more than about 10 μM; in further embodiments, compounds will exhibit an $EC_{50}$ with respect to PPAR of no more than about 5 μM; in yet further embodiments, compounds will exhibit an $EC_{50}$ with respect to PPAR of not more than about 1 μM; in yet further embodiments, compounds will exhibit an $EC_{50}$ with respect to PPAR of not more than about 200 nM, as measured in the PPAR assay described herein.

The term "selective" as used herein means having the characteristic or property of being highly specific in binding, activity, or effect. Compounds described herein as "selective for PPARδ over PPARγ," for example, may preferentially bind and/or modulate PPARδ in favor of PPARγ. Compounds described herein as "selective for PPARδ," for example, may preferentially bind and/or modulate PPARδ in favor of the γ and α isoforms. The degree of selectivity may vary, but preferably a selective compound would be at least tenfold selective for the desired target (e.g., PPAR). More preferably, the compound would be 100- to 1000-fold selective. Alternatively, a compound may be selective the sense of producing a differential effect. For example, such a compound may bind both PPARδ and PPARγ with equal or similar affinity, but activate one while inhibiting the other.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "therapeutically effective amount" as used herein refers to that amount of the compound being administered which will relieve to some extent one or more of the symptoms of the disease, condition or disorder being treated. In reference to the treatment of diabetes or dyslipidemia a therapeutically effective amount may refer to that amount which has the effect of (1) improving glucose disposal; (2) sensitizing cells to insulin; (3) normalizing lipids, e.g. triglycerides; (4) relieving to some extent (or, preferably, eliminating) one or more symptoms associated with NAFLD, NASH, or the related condition or disorder to be treated; (5) reducing hepatic inflammation; and/or (6) reducing hepatic fibrosis.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition (including, but not limited to, metabolic disorders), previous therapy, the patient's health status and response to the drugs, and the judgment of the treating physician. It is considered well within the skill of the art for one to determine such enhancing-effective amounts by routine experimentation.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure provides for compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

For example, compounds of Formula I can be contacted with p-toluenesulfonic acid to yield the p-toluenesulfonate (tosylate) salt form. Compounds of Formula 1, including Example 1 and Example 2 below, their racemates, and racemic mixtures thereof, prepared by any method can be contacted with a reagent selected from the group consisting of calcium acetate, hydrochloric acid, phosphoric acid, sulfuric acid, sodium hydroxide, potassium hydroxide, magnesium acetate, and p-toluenesulfonic acid, preferably in a 1:1 ratio, in a suitable solvent. Such solvents include but are not limited to diisopropyl ether, toluene, dichloromethane, and acetonitrile. Any technique known in the art can be used to vary conditions to induce precipitation or crystallization, including, without limitation: stifling for varying lengths of time at varying ambient conditions, the addition of hexanes or diethyl ether, evaporation, and reduction of temperature. For example, 4-[cis-2,6-dimethyl-4-(4-trifluoromethoxybenzyl)-piperazine-1-sulfonyl]-indan-2-carboxylic acid can be contacted with p-toluenesulfonic acid to yield 4-[cis-2,6-dimethyl-4-(4-trifluoromethoxy-benzyl)-piperazine-1-sulfonyl]-indan-2-carboxylic acid tosylate. The present disclosure provides for salts of each racemate of compounds of Formula I, including (S)-4-[cis-2,6-dimethyl-4-(4-trifluoromethoxy-benzyl)-piperazine-1-sulfonyl]-indan-2-carboxylic acid tosylate (Compound 2).

Other salts of compounds of Formula I may be formed. The present disclosure provides for salts of 4-[cis-2,6-dimethyl-4-(4-trifluoromethoxy-phenyl)-piperazine-1-sulfonyl]-indan-2-carboxylic acid and 4-[cis-2,6-dimethyl-4-(4-trifluoromethoxy-benzyl)-piperazine-1-sulfonyl]-indan-2-carboxylic acid, and isolated racemates of each, as provided in United States Patent Application Publication No. US2007/0093504A1, published Apr. 26, 2004, the disclosure of which is incorporated by reference as if written herein in its entirety.

While it may be possible for the compounds provided herein to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

In certain embodiments, the compounds disclosed herein may be formulated as disclosed in International Patent Application No. PCT/US07/80454, filed Oct. 4, 2007, the disclosure of which is incorporated by reference as if written herein in its entirety.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound, or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: (a) statin and/or other lipid lowering drugs for example MTP inhibitors and LDLR upregulators; (b) antidiabetic agents, e.g. metformin, sulfonylureas, or PPAR-gamma, PPAR-alpha and PPAR-alpha/gamma modulators (for example thiazolidinediones such as e.g. pioglitazone (Actos) and rosiglitazone (Avandia)); (c) antihypertensive agents such as angiotensin antagonists, e.g., telmisartan, calcium channel antagonists, e.g. lacidipine and ACE inhibitors, e.g., enalapril; (d) inhibitors of cholesterol and lipid absorption and metabolism, such as etizimibe (Zetia); and (e) other agents for the treatment of liver diseases including NASH, for example steroids such as ursodeoxycholic acid (ursodiol, Urso), chitinase and PDE inhibitors such as oxpentifylline and pentoxifylline, antioxidants such as silipide or silybin phosphatidylcholine complex, biguanides such as metformin HCl, and phytoestrogens such as silymarin.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PPAR-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of PPAR-mediated disorders.

Specific diseases to be treated by the compounds, compositions, and methods disclosed herein include liver diseases, particularly those associated with metabolic syndrome and/or fibrosis, such as NAFLD, hepatic steatosis, NASH, and cirrhosis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

The invention is further illustrated by the following examples. The examples are synthesized as provided in U.S. Published Patent App. No. 2006/0205736, pages 17-22, paragraphs 0229 through 0234, and U.S. Published Patent App. No. 2006/0167012, pages 16-22, paragraph 0218 through 0223. The disclosures of these applications are incorporated herein by reference in their entireties.

EXAMPLE 1

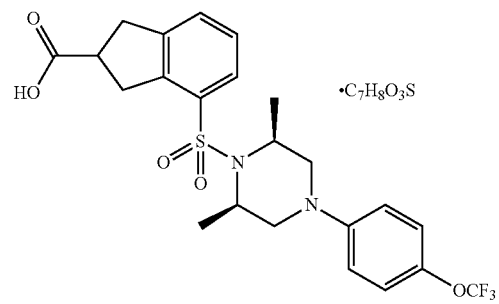 [SMILES: C[C@@H]1CN(c2ccc(OC(F)(F)F)cc2)C[C@H](C)N1S(=O)(=O)c1cccc2c1CC(C(=O)O)C2 ; "·C7H8O3S"]

(S)-4-[cis-2,6-Dimethyl-4-(4-trifluoromethoxy-phenyl)-piperazine-1-sulfonyl]-indan-2-carboxylic acid tosylate "Compound 1"

Step 1

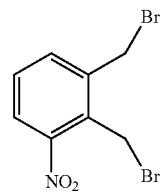

1,2-Bis(bromomethyl)-3-nitrobenzene

A 1 liter flask was charged with 1,2-dimethyl-3-nitrobenzene (20 g, 0.13 mol), N-bromosuccinimide (50 g, 0.28 mol), azobis(isobutyronitrile) (5 g, 3.0 mmol), and 200 mL of dichloromethane. This was irradiated with a 120 watt floodlamp to affect gentle reflux under nitrogen for 18 hours. The mixture was then cooled and precipitated succinimide was removed by filtration. The filtrate was concentrated and the residue was purified by chromatography on silica (5%-50% CH$_2$Cl$_2$ in hexanes) to give 2.6 g white solid (64%).

Step 2

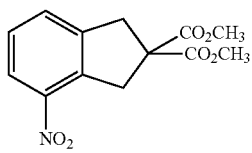 [SMILES: COC(=O)C1(C(=O)OC)Cc2cccc([N+](=O)[O-])c2C1]

Dimethyl-4-nitroindane-2,2-dicarboxylate

To a solution stirred under nitrogen at room temperature, to 5.0 mL methanol in 15.0 mL ether was added 60% sodium hydride (0.84 g, 0.021 mol) in small portions. After the addition was complete, the nearly clear and colorless solution was stirred for 5 minutes. To it was then added 1.3 g dimethyl malonate, giving a slightly cloudy colorless solution. To this was rapidly added a suspension of 3.1 g 1,2-bis(bromomethyl)-3-nitrobenzene, which immediate gave a precipitate suspended in a dark green solution. This was removed by filtration and the filtrate was concentrated. The residue was purified on silica (20%-100% CH$_2$Cl$_2$ in hexanes) to give 1.93 g off-white solid (67%).

Step 3

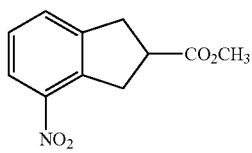

Methyl-4-nitroindane-2-carboxylate

A mixture of dimethyl-4-nitroindane-2,2-dicarboxylate (4.84 g, 0.0167 mol), lithium chloride (0.84 g, 0.0198 mol), 1.1 mL water, and 18 mL dimethylsulfoxide was heated to 160° C. under nitrogen for two hours. It was then allowed to cool and the dimethylsulfoxide was removed under high vacuum. The residue was purified on silica (10%-100% CH$_2$Cl$_2$ in hexanes) to give 2.5 g white solid (65%).

Step 4

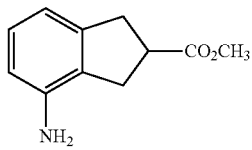

Methyl-4-aminoindane-2-carboxylate

A mixture of methyl-4-nitroindane-2-carboxylate (2.4 g, 0.11 mol) and 10% palladium on carbon (1.1 g, 0.01 mol) in ethyl acetate (15 mL) was shaken under 55 PSI hydrogen for 1 hour. It was then filtered and the filtrate was concentrated to give 2.07 g white solid (100%).

Step 5

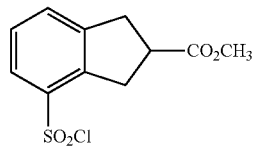

Methyl 4-chlorosulfonyl-indan-2-carboxylate

A mixture of methyl-4-aminoindane-2-carboxylate (2.5 g, 0.013 mol), 12.5 mL acetonitrile, and 12.5 mL H$_2$O was cooled to −5° C. in an ice-salt bath. To this was added 2.6 mL concentrated HCl (0.014 mol). To this was added dropwise over 20 minutes a solution of 1.0 g sodium nitrite (0.021 mol) in 5 mL water. After the addition was complete the solution was stirred for 20 minutes. It was then transferred to a jacketed addition funnel cooled with ice water. The solution was added dropwise to a solution stirred under nitrogen at 55° C. of 4.2 g potassium thioxanthate (0.026 mol) in 20 mL H$_2$O. As the addition took place, a dark layer rose to the top of the diazonium ion solution which was not added. After the addition was complete the mixture was stirred at 55° C. for 30 minutes, then was allowed to cool and was extracted with 40 mL ethyl acetate. The organic layer was dried (MgSO$_4$) and concentrated. The residue was loaded on 80 mL silica gel which was slurry-packed in hexanes. This was eluted with 100 mL hexanes, then 1%-50% CH$_2$Cl$_2$ in hexanes in 50 mL fractions to give 1.3 g amber oil (33%). A mixture of 3.6 g of the above compound in 30 mL CCl$_4$ and 10 mL H$_2$O was vigorously stirred and cooled to 3 C. Chlorine gas was bubbled through at such a rate that the temperature stayed below 10° C. After conversion was complete, the phases were separated and the aqueous layer was extracted with CH$_2$Cl$_2$. The combined organic layers were dried (MgSO$_4$) and concentrated to give 4.0 g yellow oil (100%).

Step 6

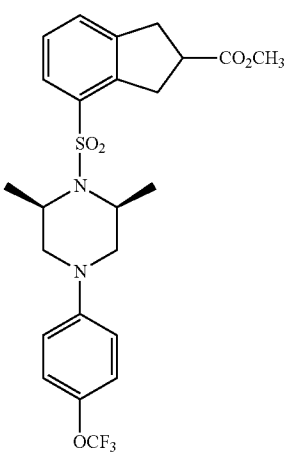 [SMILES: COC(=O)C1Cc2cccc(S(=O)(=O)N3[C@H](C)CN(c4ccc(OC(F)(F)F)cc4)C[C@@H]3C)c2C1]

4-[cis-2,6-Dimethyl-4-(4-trifluoromethoxy-phenyl)-piperazine-1-sulfonyl]-indan-2-methyl ester A mixture of methyl 4-chlorosulfonyl-indan-2-carboxylate (2.13 g, 0.0078 mol) obtained from Step 6, cis-3,5-dimethyl-1-(4-trifluoromethoxy-phenyl)-piperidine (3.0 g, 0.0109 mol) obtained from Example 51, mL acetonitrile, and 3.0 g $K_2CO_3$ (0.0217 mol) was heated to 60° C. under nitrogen with stifling for 20 hours. It was then filtered and the filtrate was concentrated. The residue was purified by chromatography on silica (5%-50% EtOAc in hexanes) to give 2.64 g viscous yellow oil (66%).

Step 7

4-[cis-2,6-Dimethyl-4-(4-trifluoromethoxy-phenyl)-piperazine-1-sulfonyl]-indan-2-carboxylic acid To a solution of 4-[cis-2,6-dimethyl-4-(4-trifluoromethoxy-phenyl)-piperazine-1-sulfonyl]-indan-2-methyl ester (2.64 g, 0.0052 mol) in the minimum amount of THF (ca 15 mL) was added a solution of 0.14 g LiOH (0.0057 mol) in the minimum amount of water (ca 2.5 mL). This was capped and stirred at room temperature for 12 hours. Examination by HPLC showed the reaction was 85% complete so an additional 0.020 g LiOH (0.125 eq total) was added and stirring was continued for 3 hours. It was then concentrated to remove THF and partitioned between EtOAc and water. The aqueous layer was treated with 0.54 mL conc. HCl. It was then extracted with ethyl acetate. The organic layer was dried ($MgSO_4$) and concentrated to give 2.38 g yellow amorphous solid (93%).

Step 8

(S)-4-[cis-2,6-Dimethyl-4-(4-trifluoromethoxy-phenyl)-piperazine-1-sulfonyl]-indan-2-carboxylic acid A single enantiomer of 4-[cis-2,6-dimethyl-4-(4-trifluoromethoxy-phenyl)-piperazine-1-sulfonyl]-indan-2-carboxylic acid was obtained by chiral HPLC (chiralpak ASH 0.46×15 cm Hex/IPA 94:6 (v/v) with 0.1% TFA, flow rate 1 ml/min) separation from the racemate. LCMS 497.1 (M−1). Formation of p-Toluenesulfonate Salt:

(S)-4-[cis-2,6-Dimethyl-4-(4-trifluoromethoxy-phenyl)-piperazine-1-sulfonyl]-indan-2-carboxylic acid and p-toluenesulfonic acid were combined in a 1:1 molar ratio in tetrahydrofuran (THF) solvent. No precipitation occurred. The clear solution was chilled in an ice water bath and allowed to evaporate under a dry nitrogen purge, yielding off-white solids.

Alternate direct preparation of (S)-4-[cis-2,6-dimethyl-4-(4-trifluoromethoxy-phenyl)-piperazine-1-sulfonyl]-indan-2-carboxylic acid tosylate

Step 1

32% HCl is added to a solution of sodium nitrite in water and acetonitrile at 0° C. The solution is cooled to −5° C. and a solution of (R,S)-4-amino-indan-2-carboxylic acid methyl ester hydrochloride in water, acetonitrile, and 32% HCl is added, keeping the temperature between −7 and −10° C. The resulting cold diazonium solution is added to a solution of potassium ethylxanthogenate, in water and acetonitrile, at 60° C. After heating at 60° C., the mixture is cooled to room temperature and extracted from dichloromethane. The organic solution is charged into the reactor and concentrated under reduced pressure. Dichloromethane and water are added, the mixture cooled to 5° C., and chlorine gas passed through the mixture. The organic solution is separated and the aqueous solution is extracted from dichloromethane. The combined organic solution is dried over magnesium sulfate and concentrated under reduced pressure to afford (R,S)-4-chlorosulfonyl-indan-2-carboxylic acid. HPLC may be used to monitor the reaction.

Step 2

Potassium carbonate is added to a mixture of cis-3,5-dimethyl-1-(4-trifluoromethoxy-phenyl)-piperazine hydrochloride in dichloromethane and water. After stifling at room temperature, the organic phase is collected and the aqueous layer extracted from dichloromethane. The combined organic solution is charged into the reactor and concentrated under reduced pressure, followed by the addition of acetonitrile and potassium carbonate. A solution of (R,S)-4-chlorosulfonyl-indan-2-carboxylic acid, in acetonitrile, is added to the reaction mixture. After heating at 50° C., the reaction mixture is cooled to 20° C. The mixture is transferred into a 200 L movable agitation feed tank, which is charged with Celite, and the suspension is stirred. The suspension is filtered, filter cake washed with acetonitrile, and the filtrate is concentrated under reduced pressure, cooled to 0-5° C., and 32% HCl added. Following further concentration and filtration, the filtrate is concentrated to give an oil which is purified by silica gel chromatography and recrystallized from isopropanol to give the product (R,S)-4-[cis-2,6-dimethyl-4-(4-trifluoromethoxy-phenyl)-piperazine-1-sulfonyl]-indan-2-carboxylic acid methyl ester (>95% by HPLC).

Step 3

Simulated moving bed (SMB) chromatography was used to separate the S- and R-enantiomers of (R,S)-4-[cis-2,6-dimethyl-4-(4-trifluoromethoxy-phenyl)-piperazine-1-sulfonyl]-indan-2-carboxylic acid methyl ester. The SMB method uses a Chiralpak AS column and heptane/isopropanol (1:1 v/v) to yield the S-enantiomer, (S)-4-[cis-2,6-dimethyl-4-(4-trifluoromethoxy-phenyl)-piperazine-1-sulfonyl]-indan-2-carboxylic acid methyl ester (>99.0% by chiral HPLC).

Step 4

To a solution of (S)-4-[cis-2,6-dimethyl-4-(4-trifluoromethoxy-phenyl)-piperazine-1-sulfonyl]-indan-2-carboxylic acid methyl ester, in THF, is added a solution of lithium hydroxide in water, which is stirred at 20° C. and concentrated under reduced pressure. The reaction mixture is cooled to 9° C., neutralized with 32% HCl, and extracted from toluene. Water is removed from the organic solution by azeotropic distillation. Following distillation, the organic solution is cooled to ambient temperature and transferred to a feeding vessel. The reactor is charged with p-toluenesulfonic acid in toluene and water is removed by azeotropic distillation. The solution is cooled to 60° C., followed by the addition of the organic solution from the feeding vessel. The mixture is stirred at 83° C., then cooled to 10° C. to induce crystallization. The product suspension is filtered, the filter cake rinsed with heptane, and dried on a rotovap, at 40° C., to afford (S)-4-[cis-2,6-dimethyl-4-(4-trifluoromethoxy-phenyl)-piperazine-1-sulfonyl]-indan-2-carboxylic acid tosylate, Compound 1. $^1$HNMR δ 1.60 (d), 1.62 (d), 2.33 (s), 3.23 (m), 3.49 (m), 3.39 (m), 4.05 (m), 4.49 (m), 3.40 (dd), 3.23 (dd), 7.14 (d), 7.14 (d), 7.09 (d), 7.09 (d), 7.59 (d), 7.59 (d), 7.71 (d), 7.26, dd, 7.57 (d), 7.57 (d), 7.40 (d).

EXAMPLE 2

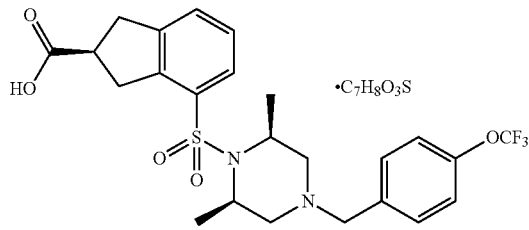 [SMILES: C[C@@H]1CN(Cc2ccc(OC(F)(F)F)cc2)C[C@H](C)N1S(=O)(=O)c1cccc2c1C[C@@H](C(=O)O)C2 ; "·C7H8O3S"]

(S)-4-[cis-2,6-Dimethyl-4-(4-trifluoromethoxy-benzyl)-piperazine-1-sulfonyl]-indan-2-carboxylic acid tosylate "Compound 2"

Step 1

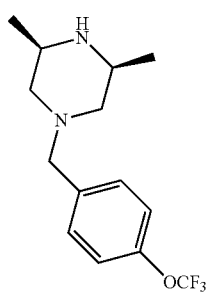 [SMILES: C[C@@H]1CN(Cc2ccc(OC(F)(F)F)cc2)C[C@H](C)N1]

cis-3,5-Dimethyl-1-(4-trifluoromethoxy-benzyl)-piperazine

To a solution of 4-(trifluoromethoxy)-benzaldehyde (776 uL, 4.38 mmol) in methylene chloride (30 mL) was added cis-2,6-dimethyl piperazine (1.0 g, 8.77 mmol). After 1 hour sodium triacetoxy borohydride (2.45 g, 8.77 mmol) was added to the mixture. The solution was stirred at room temperature for an additional 4 hours. The reaction was concentrated in vacuo, diluted with ethyl acetate and extracted with 1N HCl (2×50 mL). The aqueous layer was then neutralized with NaOH and extracted with ethyl acetate (3×50 mL). The organic layer was dried ($Na_2SO_4$) and concentrated to provide cis-3,5-dimethyl-1-(4-trifluoromethoxy-benzyl)-piperazine (1.01 g, 80%). $^1$H NMR (400 MHz, $CD_3OD$) δ 7.42 (d, 2H), 7.23 (d, 2H), 3.54 (s, 2H), 2.98-2.88 (m, 2H), 2.82-2.74 (m, 2H), 1.69 (t, 2H), 1.05 (d, 6H); LCMS 289.5 (M+1)$^+$.

Step 2

4-[cis-2,6-Dimethyl-4-(4-trifluoromethoxy-benzyl)-piperazine-1-sulfonyl]-indan-2-carboxylic acid The compound 4-[cis-2,6-dimethyl-4-(4-trifluoromethoxyl-benzyl)-piperazine-1-sulfonyl]-indan-2-carboxylic acid was synthesized according to the procedure in Example 1 using cis-3,5-dimethyl-1-(4-trifluoromethoxy-benzyl)-piperazine. $^1$H NMR (400 MHz, $CD_3OD$) δ 7.74-7.64 (m, 4H), 7.47 (d, 1H), 7.39-7.28 (m, 2H), 4.42 (s, 2H), 4.21-2.18 (m, 2H), 3.50-3.34 (m, 5H), 3.33-3.19 (m, 4H), 1.56 (d, 6H); LCMS 497.5 (M+1)$^+$.

Step 3

(S)-4-[cis-2,6-Dimethyl-4-(4-trifluoromethoxy-benzyl)-piperazine-1-sulfonyl]-indan-2-carboxylic acid A single enantiomer of 4-[cis-2,6-Dimethyl-4-(4-trifluoromethoxy-benzyl)-piperazine-1-sulfonyl]-indan-2-carboxylic acid was obtained with the following protocol. The product from Example 2 Step 1 and the product from Example 1 Step 5 were reacted using the conditions outlined in Example 1 Step 6 to yield the racemic methyl ester. Chiral separation using OJ-H, 25% methanol in $CO_2$ (100 bar), 5 mL/min followed by hydrolysis using conditions outlined in Example 1 Step 7 provided a single enantiomer of 4-(cis-2,6-dimethyl-4-(3-trifluoromethoxy)benzyl)piperazin-1-yl-sulfonyl)-2,3-dihydro-1H-indene-2-carboxylic acid. $^1$H NMR (400 MHz, $CD_3OD$) δ 7.66 (d, 1H), 7.46 (d, 1H), 7.41 (d, 2H), 7.36-7.30 (m, 1H), 7.19 (d, 2H), 4.08-3.99 (m, 1H), 3.94-3.8 (m, 1H), 3.56-3.49 (m, 2H), 3.43 (s, 2H), 3.40-3.22 (m, 3H), 2.57 (t, 2H), 2.09-1.92 (m, 2H), 1.56 (d, 6H); LCMS 513.5 (M+1)$^+$.

Formation of p-Toluenesulfonate Salt:
(S)-4-[cis-2,6-Dimethyl-4-(4-trifluoromethoxy-benzyl)-piperazine-1-sulfonyl]-indan-2-carboxylic acid tosylate can be made in a manner analogous to either of the two disclosed for Example 1 above.

Alternate direct preparation of (S)-4-[cis-2,6-dimethyl-4-(4-trifluoromethoxy-phenyl)-piperazine-1-sulfonyl]-indan-2-carboxylic acid tosylate

Step 1a

A 600 L reactor (reactor 1) was purged with nitrogen and charged with (R,S)-4-amino-indan-2-carboxylic acid methyl ester hydrochloride (22.0 kg). Water (87 L), acetonitrile (83 L), and 33% HCl (16.5 kg) were then charged into the reactor. A second 600 L reactor (reactor 2) was purged with nitrogen and charged with sodium nitrite (7.33 kg), water (67 L) and acetonitrile (68 L). Reactor 2 was cooled to 0° C. 33% HCl (5.6 kg) was added to reactor 2 and the reaction solution was cooled to −8° C. The solution in reactor 1 was transferred into reactor 2 over 7 h with the internal temperature kept between −6 and −9° C. The resulting mixture was stirred for 1 h. Potassium ethyl xanthogenate (38.7 kg) was charged into reactor 1 (previously cleaned). Water (74 L) and acetonitrile (74 L) were charged into the reactor. The resulting solution was heated to 60° C. The cold diazonium solution in reactor 2 was added to the warm mixture in reactor 1 over 135 min. Following the addition, the reaction mixture was heated at 60° C. for 50 min. The mixture was cooled to room temperature and extracted from dichloromethane (3×74 L). The combined organic solution was washed with brine (37 L) and water (37 L), and solvent (325 L) was removed under reduced pressure.

Step 1b was separated into two batches.

Step 1b, Batch 1

One quarter of the concentrated reaction mixture from Step 1a (23.06 kg) was charged into a 160 L reactor. An additional 20 L of solvent was removed under reduced pressure and methanol (10 L) was added to the reaction mixture. The operation was repeated; solvent (9 L) was removed under reduced pressure and methanol (10 L) was added to the reaction mixture. The operation was repeated again; solvent (10 L) was removed under reduced pressure and methanol (36 L) was added to the reaction mixture. The reaction mixture was cooled to 0° C. Sodium methoxide (4.67 kg of a 30% solution in methanol) was added to the reaction mixture over 35 min. Following the addition, the reaction mixture was stirred at 3° C. for 30 min. Methanol (10 L) was added and diluted $O_2$ (5% in $N_2$) was bubbled through the reaction solution while acetic acid (1.01 kg) was added. The gassing was continued overnight at 0° C. and then for another 24 h. The gassing was stopped and the reactor was purged with $N_2$. The suspension was heated to 60° C. and stirred for 10 min at which time a solution was obtained. The reaction solution was cooled to 45° C. and stirred for 45 min until crystallization commenced. The suspension was cooled to 10° C. and stirred for 2.5 h. The solid was collected by filtration and rinsed with methanol (3×5.5 L). The filter cake was dried to give (R,S)-4,4'-Disulfanediylbis-indan-2-carboxylic acid dimethyl ester (1.75 kg).

Step 1b, Batch 2

Three quarters of the concentrated reaction mixture from Step 1a (69 kg) was charged into a 160 L reactor. An additional 63 L of solvent was removed under reduced pressure and methanol (27.8 L) was added to the reaction mixture. The operation was repeated; solvent (28 L) was removed under reduced pressure and methanol (27.8 L) was added to the reaction mixture. The operation was repeated again; solvent (26 L) was removed under reduced pressure and methanol (109 L) was added to the reaction mixture. The reaction mixture was cooled to 1° C. Sodium methoxide (13.1 kg of a 30% solution in methanol) was added to the reaction mixture over 40 min. Following the addition, the reaction mixture was stirred at 4° C. for 10 min. Diluted $O_2$ (5% in $N_2$) was bubbled through the reaction solution while acetic acid (3.04 kg) was added. The gassing was continued overnight at 0° C. and then for another 24 h. Additional acetic acid (0.22 kg) was added and the gassing was continued another 24 h at 0° C. The gassing was stopped and the reactor was purged with $N_2$. The suspension was heated to 58° C. and stirred for 10 min at which time a solution was obtained. The reaction solution was cooled to 47° C. and stirred for 2 min until crystallization commenced. The suspension was cooled to 12° C. and stirred for 2.5 h. The solid was collected by filtration and rinsed with methanol (3×16.5 L). The filter cake was dried to give (R,S)-4,4'-Disulfanediylbis-indan-2-carboxylic acid dimethyl ester (6.9 kg). Total yield of (R,S)-4,4'-Disulfanediylbis-indan-2-carboxylic acid dimethyl ester (8.65 kg, 43%).

Step 2 was separated into two batches.

Step 2, Batch 1

A 160 L reactor was purged with nitrogen and charged with (R,S)-4,4'-Disulfanediylbis-indan-2-carboxylic acid dimethyl ester (1.714 kg). Acetic acid (17 L) was charged into the reactor and the reaction mixture was heated at 59° C. for 10 min until a solution was obtained. Water (3.4 L) was charged into the reactor and the reaction mixture was cooled to −3° C. Sodium hypochlorite (6.274 kg of a 12.8% NaOCl solution in water) was added over 115 min with the internal temperature kept between −3 and −11° C. The reaction mixture was stirred for 30 min at −11° C. and (R,S)-4-Chlorosulfonyl-indan-2-carboxylic acid methyl ester seed crystals (8.6 g) were added. A second portion of sodium hypochlorite (9.413 kg of a 12.8% NaOCl solution in water) was added over 90 min with the internal temperature kept between −11 and −15° C. The reaction mixture was stirred for 105 min between −11 and −14° C. A third portion of sodium hypochlorite (0.787 kg of a 12.8% NaOCl solution in water) was added over 2 min with the internal temperature kept between −14° C. The reaction mixture was stirred for 13 min and water (9 L) was added over 30 min. The reaction mixture was stirred an additional 30 min at −12° C. and the suspension was filtered. The filter cake was washed with water (2×3.4 L) and heptane (2×3.4 L). The filter cake was dried to give (R,S)-4-Chlorosulfonyl-indan-2-carboxylic acid methyl ester (1.732 kg).

Step 2, Batch 2

A 160 L reactor was purged with nitrogen and charged with (R,S)-4,4'-Disulfanediylbis-indan-2-carboxylic acid dimethyl ester (6.846 kg). Acetic acid (69 L) was charged into the reactor and the reaction mixture was heated at 55° C. for 5 min until a solution was obtained. Water (14 L) was charged into the reactor and the reaction mixture was cooled to −7° C. Sodium hypochlorite (19 L of a 13.4% NaOCl solution in water) was added over 160 min with the internal temperature kept between −2 and −10° C. The reaction mixture was stirred for 20 min at −2° C. and (R,S)-4-Chlorosulfonyl-indan-2-carboxylic acid methyl ester seed crystals (34.2 g) were added. A second portion of sodium hypochlorite (28 L of a 12.8% NaOCl solution in water) was added over 139 min with the internal temperature kept between −4 and −6° C. The reaction mixture was stirred for 31 min between −4 and −7° C. A third portion of sodium hypochlorite (2.985 kg of a 13.4% NaOCl solution in water) was added. Water (37.5 L) was added over 50 min. The reaction mixture was stirred for 110 min at −8° C. and the suspension was filtered. The filter cake was washed with water (2×14 L) and heptane (3×14 L). The filter cake was dried to give (R,S)-4-Chlorosulfonyl-indan-2-carboxylic acid methyl ester (6.073 kg).

(R,S)-4-Chlorosulfonyl-indan-2-carboxylic acid methyl ester from Batch 1 (1.732 kg) and Batch 2 (6.073 kg) were combined and charged into the reactor. The reactor was charged with dichloromethane (36 L) and a mixture of water (20 L), sodium chloride (2.134 kg) and 33% HCl (2.135 kg). The reaction mixture was cooled to −2° C. and sodium hypochlorite (2.508 kg of a 12.8% NaOCl solution in water) was added over 15 min with the internal temperature kept between −1 and −2° C. The reaction mixture was stirred for 30 min between −1 and −4° C. Stirring was stopped and the phases were separated. The organic layer was charged back into the reactor and washed with water (2×19 L). The reaction mixture was concentrated under reduced pressure. Heptane (4 L) and (R,S)-4-Chlorosulfonyl-indan-2-carboxylic acid methyl ester seed crystals (3.8 g) were added to the resulting oil. The reaction mixture was stirred for 30 min until a suspension was obtained. The solid was collected by filtration and dried to give (R,S)-4-Chlorosulfonyl-indan-2-carboxylic acid methyl ester (7.542 kg, 66% yield).

Step 3

A 160 L reactor was purged with nitrogen and charged with acetonitrile (72 L). cis-3,5-Dimethyl-1-(4-trifluoromethoxy-benzyl)-piperazine hydrochloride (6.21 kg) and (R,S)-4-Chlorosulfonyl-indan-2-carboxylic acid methyl ester (3.5 kg) were added to the reactor. Triethylamine (3.87 kg) was added over 30 min and the reaction mixture was stirred at room temperature for 58 h. Citric acid (1.96 kg) was added and the reaction mixture stirred for 10 min. Water (71 L) was added over 45 min and the reaction mixture was stirred for 30 min. The suspension was filtered and the filter cake was washed with water (2×11 L) and dried to give C-20350 (4.67 kg, 69% yield).

Step 4

Simulated moving bed (SMB) chromatography was used to separate the S- and R-enantiomers of (R,S)-4-[cis-2,6-Dimethyl-4-(4-trifluoromethoxy-benzyl)-piperazine-1-sulfonyl]-indan-2-carboxylic acid methyl ester. The SMB method uses a Chiralcel OJ column and a mobile phase of methanol/diethylmethylamine (100:0.1, v:v). The SMB separation of (R,S)-4-[cis-2,6-Dimethyl-4-(4-trifluoromethoxy-benzyl)-piperazine-1-sulfonyl]-indan-2-carboxylic acid methyl ester (4.64 kg) gave the S-enantiomer, (S)-4-[cis-2,6-Dimethyl-4-(4-trifluoromethoxy-benzyl)-piperazine-1-sulfonyl]-indan-2-carboxylic acid methyl ester, in two portions with a chiral purity of 98.68 and 99.12% respectively. Total yield of (S)-4-[cis-2,6-Dimethyl-4-(4-trifluoromethoxy-benzyl)-piperazine-1-sulfonyl]-indan-2-carboxylic acid methyl ester, 2.18 kg, 47%.

Step 5

A 100 L reactor was purged with nitrogen and charged with THF (16 L). (S)-4-[cis-2,6-Dimethyl-4-(4-trifluoromethoxy-benzyl)-piperazine-1-sulfonyl]-indan-2-carboxylic acid methyl ester (2.1 kg) was added to the reactor. The reactor was charged with lithium hydroxide (0.184 kg) and water (2 L), and the mixture was stirred at room temperature for 12 h. Solvent (15 L) was removed under reduced pressure and the reaction mixture was transferred into a feed tank. p-Toluenesulfonic acid (1.672 kg) was dissolved in water (8 L) and charged into the reactor as a solution. The solution was heated to 69° C. and (S)-4-[cis-2,6-Dimethyl-4-(4-trifluoromethoxy-benzyl)-piperazine-1-sulfonyl]-indan-2-carboxylic acid tosylate salt seed crystals (4.24 g) were added to the solution. The reaction mixture in the feed tank was added to the reactor over 2.5 h. The reaction mixture was heated at 69° C. for 1 h and then cooled to room temperature overnight. The suspension was filtered and the filter cake was washed with water (2×4 L) and dried to give a mixture of the hydrate, C-021064, and the desired polymorph, (S)-4-[cis-2,6-Dimethyl-4-(4-trifluoromethoxy-benzyl)-piperazine-1-sulfonyl]-indan-2-carboxylic acid tosylate salt. The reactor was flushed with nitrogen and charged with t-BuOH (32 L). The dried filter cake was added to the reactor and the suspension was heated to reflux at 81° C. at which time all the solids had gone into solution. The solution was cooled to 28° C. over 5 h. The resulting suspension was filtered and the filter cake was washed with t-BuOH (2 L) and dried to give (S)-4-[cis-2,6-Dimethyl-4-(4-trifluoromethoxy-benzyl)-piperazine-1-sulfonyl]-indan-2-carboxylic acid tosylate salt (Compound 2, 2.005 kg, 73%).

EXAMPLE 3

In Vitro Biological Activity

Examples 1 and 2 have been shown to be PPAR modulators in United States Patent Application Publications No. US2006/0167012A1, published Jul. 27, 2006, and US2006/0205736A1, published Sep. 14, 2006.

EXAMPLE 4

Early Steatosis Model Materials and Methods In Vivo Experimental Set Up

NASH is a complex disease and facets of human NASH are recapitulated in rodent species. Art-recognized rodent models of NASH include the carbon tetrachloride ($CCL_4$)-induced liver injury model, bile-duct ligation induced liver injury model and finally, methionine and choline deficient (MCD) diet-induced liver injury model. However, none of these models truly represent features that are characteristic of human NASH, which is characterized by: (1) elevated serum transaminases, AST and ALT, (2) hepatic steatosis, (3) hyperinsulinemia, (4) hepatic inflammation and (5) centrilobular fibrosis, a manifestation of mesenchymal transition of hepatic stellate cells. Therefore, a rodent DIO model was developed that simulated several features of human NASH. These features are treated individually below.

Early Steatosis Model: C57B1/6J mice (22-39 days old) mice were used for the study. Mice were fed normal chow food (Lab Diet, 5P14Prolab Animal Diet, PMI Nutritional International, Brentwood, Mo., Cat# RMH 2500) or 58% high fat diet (HFD, 58 kcal % fat and corn starch with purple dye, Research Diets, New Brunswick, N.J., Cat# D12330 equivalent to Western diet) for 120-150 days. Analyses of body weights demonstrated that one fifth of the mice on HFD did not gain any significant body weight or liver fatty tissue (LFT) and had normal plasma insulin levels. This group is referred to as the HFD-low body group in FIG. 1A (insulin & liver fat accumulation~normal). On the other hand, one fifth of the mice gained 60-70% higher body weight (compared to normal chow fed mice) while on the same HFD diet (NASH group, very high insulin and liver fat) further shown in FIG. 1A. The majority of the mice (three fifths) gained body weight as expected on the HFD (30-40% higher than the normal chow fed mice) and is referred to as the DIO group (normal to moderately high insulin and liver fat accumulation) as shown in FIG. 1A. Control animals (n=5) representative of the HFD-low body weight and the NASH groups were sacrificed prior to starting the rest of the animals on treatment with the Compound 2 (5 or 10 mg/Kg/day). Liver, white adipose and muscle from the sacrificed mice were collected for histology performed on the liver tissue.

Evaluation of clinical chemistry among the different body weight clusters (n=6 per group) demonstrated that the NASH mice also demonstrated the markedly elevated liver transaminases AST and ALT (see Table 1 below and FIG. 1D1) that serve as markers of liver damage.

Figure 1C:
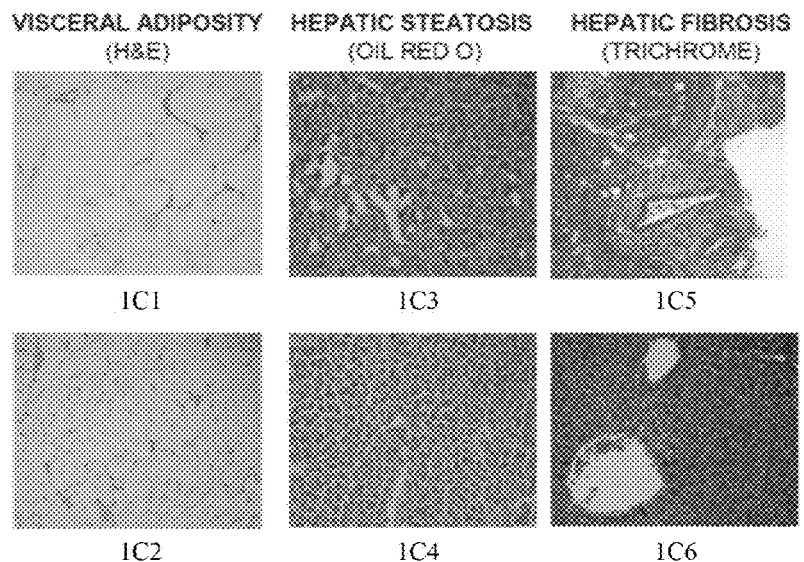
FIG. 1C represents the morphological differences between adipose and liver tissue taken from NASH (top row, LFT and insulin elevated) versus normal (bottom, LFT and insulin normal) mice.
Figure 1D:
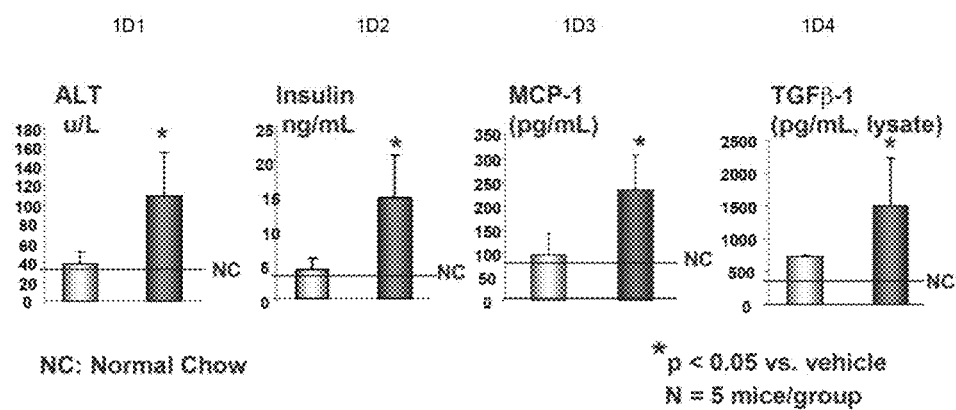
FIG. 1D depicts additional features used to make a diagnosis of NASH in the murine model: elevated alanine aminotransferase (ALT) in NASH vs. HFL mice (FIG. 1D1); elevated insulin in NASH vs. HFL mice (FIG. 1D2); and elevated inflammatory markers MCP-1 (monocyte chemotactic protein 1) and TGF-β (transforming growth factor β) in NASH mice vs. HFL mice (FIGS. 1D3 and 1D4). In each of subfigures 1D1-1D4, comparable levels in NC mice are also shown as a line.
Figure 2A:
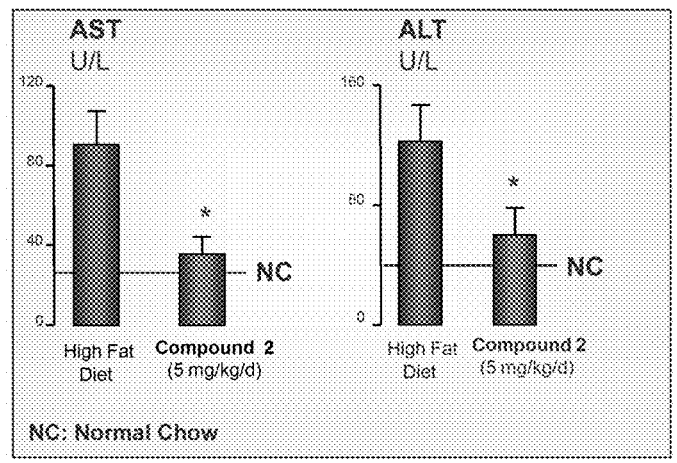
FIG. 2A shows a comparison of AST (aspartate aminotransferase) and ALT (alanine aminotransferase) levels as between HFD mice either administered the compound of Example 2 (Compound 2, 42 days of 5 mg/kg/day), or vehicle. Comparable mean levels of AST and ALT in NC mice are also shown as a line.

Inflammation is a key feature that promotes progression of hepatic steatosis stage of NAFLD to the NASH stage. Hyperinsulinemia, hyperleptinemia, elevated levels of circulating adipokines (leptin and resistin) as well as proinflammatory chemokines and cytokines play a critical role in this process. Fasting insulin levels were significantly higher in the NASH group, as evidenced in Table 1 and FIG. 1D2. Proinflammatory marker monocyte chemoattractant protein (MCP-1), which functions as a chemoattractant factor for the infiltration of monocytes into an injured tissue, was elevated in peripheral circulation in the NASH group was, as shown in FIG. 1D3. Leptin, an adipokine that is required for hepatic stellate cell activation and progression of hepatic steatosis to NASH, was not significantly elevated in NASH mice in the study, and data is therefore not reported. (n=6 mice per group.)

TABLE 1

| Criteria | NC | NASH |
|---|---|---|
| Elevated Serum Transaminases, U/L | ALT—31 ± 0.5 AST—48 ± 4 | ALT—89 ± 8.5* AST—118 ± 9* |
| Fasting Hyperinsulinemia, mg/dL | 119 ± 21 | 184 ± 15 |
| Inflammatory Marker (Plasma MCP-1), pg/mL | ~52 ± 4 | ~100 ± 7 |
| Body Weight of Age >6 Months, g | ~31 ± 0.5 | ~51 ± 0.2* |
| Lipid Accumulation in liver tissue (Triglyceride Levels), μg/mg | 6 ± 3 | 40 ± 12 |
| Fibrosis | No evidence of fibrosis; normal inflammatory markers such as TGFβ-1 | Histological evidence of fibrosis and elevated inflammatory markers such as TGFβ-1 |

Figure 4A:
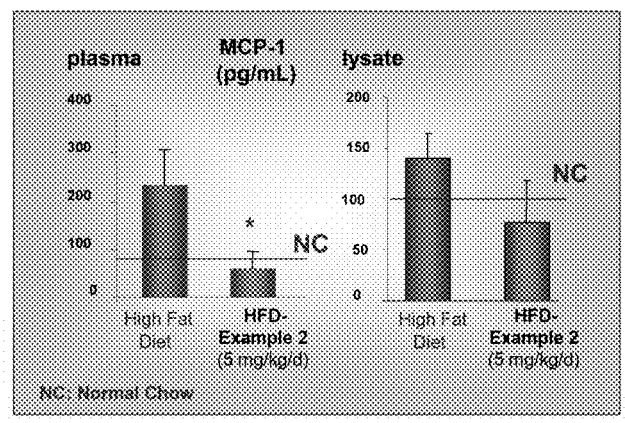
FIG. 4A shows a comparison of MCP-1 in plasma and lysate as between HFD mice either administered the compound of Example 2 (Compound 2, 42 days of 5 mg/kg/day), or vehicle. Comparable mean levels of MCP-1 in NC mice are also shown as a line.
Figure 4B:
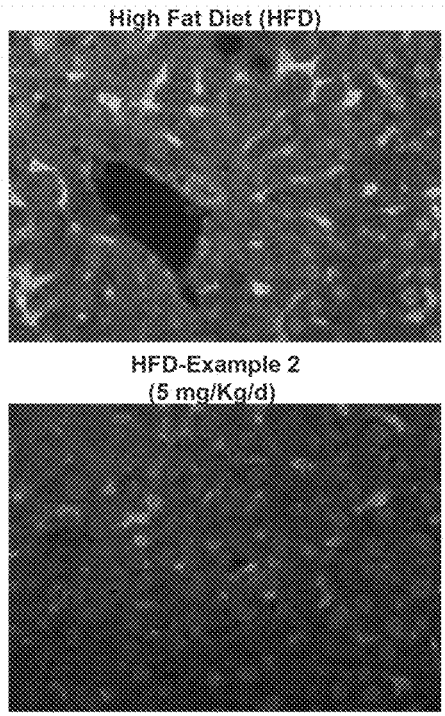
FIG. 4B is a comparison of the macrophage accumulation as seen in histological images from the livers of HFD mice either administered the compound of Example 2 (Compound 2, 42 days of 2 mg/kg/day, bottom image) or vehicle (top image).

Inflammation in the liver also promotes expression and activation of the profibrotic TGFβ pathway. Activation of TGFβ induces expression of its downstream target connective tissue growth factor (CTGF), a potent profibrotic cytokine that amplifies the prosclerotic effects of TGFβ. CTGF binds to $\alpha_v\beta_3$ integrin expressed on the hepatic stellate cells and recruits heparin sulfate proteoglycan (HSPG) to stimulate fibrosis via the activation of the MAPK pathway and transcription factor CREB. With this background, TGFβ-1 was selected as a profibrotic inflammatory marker for monitoring as between NC and NASH subjects, and was shown to be elevated in NASH vs. NC mice (n=6 per group), as shown in FIG. 1D4.

Figure 5:
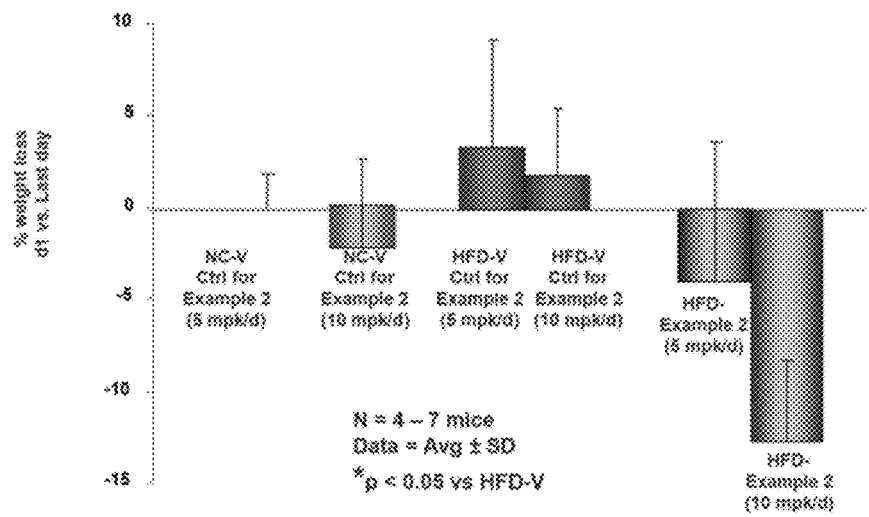
Figure 6A:
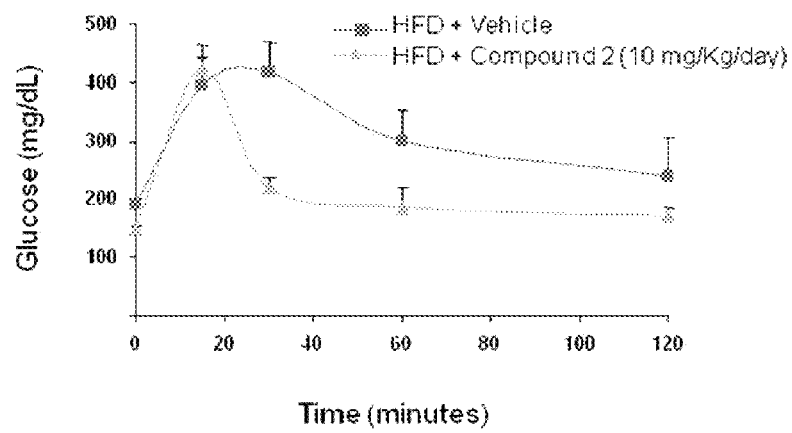
FIG. 6A shows the difference in glucose disposal as between HFD mice either administered the compound of Example 2 (Compound 2, 21 days of 5 mg/kg/day), or vehicle.
Figure 6B:
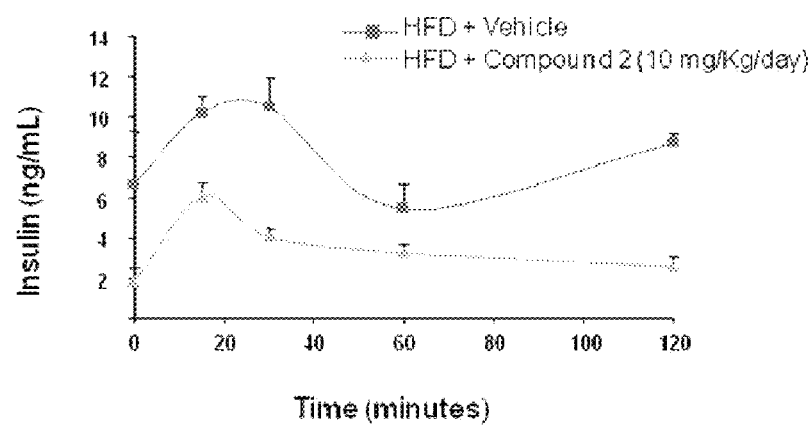
FIG. 6B shows the difference in peripheral insulin sensitivity as between HFD mice either administered the compound of Example 2 (Compound 2, 21 days of 5 mg/kg/day), or vehicle.

The development of NASH was further confirmed using histological analyses of liver. The sections were analyzed for 1) hepatic steatosis 2) necroinflammation, and 3) fibrosis. Histological analyses of hepatic steatosis was assessed by quantitative image analysis of Oil Red O stain in liver sections and defined as the percentage of Oil Red 'O' positive area relative to the total image area. The NASH group demonstrated significant steatosis compared to the NC group (47.7% vs. 1.7% respectively; p<0.0005; n=4 per group) as evidenced by percent field area occupied by stained oil deposits. The hepatic tissue from NASH mice showed severe distortion or even the loss of histological architecture (FIGS. 1C3 and 1C4). Histological evaluation of fibrosis was conducted in formalin fixed liver sections from the NASH mice and confirmed using the Trichrome staining technique demonstrated that the NASH mice show clear evidence of hepatic fibrosis compared to NC mice (FIGS. 1C5 and 1C6).

Fold changes in expression of genes involved in fibrosis and matrix remodeling in the liver were also investigated. mRNA was isolated from the liver of 4 mice from each group and gene expression was analyzed using Affynmatrix microarray followed by GOBY software analyses. Data represents average fold change in gene expression in the NASH over NC group. These gene array analyses demonstrated selective upregulation of genes involved in matrix remodeling and formation (Collagen, Fibronectin, Vimentin and Connective Tissue Growth factor—CTGF), as well as genes involved in inhibition of matrix degradation (Timp 1 and Timp 2), as shown in Table 2.

TABLE 2

| Fibrosis and matrix promoting genes | Fold change over NC |
|---|---|
| Col1a1 | 12.3 |
| Col1a2 | 3.1 |
| Col3a1 | 3.4 |
| Col5a2 | 4.1 |
| Col6a2 | 14.4 |
| Vimentin | 2.9 |
| Fibronectin | 2.4 |
| Timp 1 | 1.6 |
| Timp 2 | 6.2 |
| CTGF | 2.9 |

Fold changes in expression of genes involved in cell death, DNA and oxidative damage in the liver of NASH group compared to the NC group were also investigated. mRNA was isolated from the liver of 4 mice from each group and gene expression was analyzed using Affynmatrix microarray followed by GOBY software analyses. Data represents average fold change in gene expression in the HFD-NASH/NC group. These gene array analyses demonstrated selective upregulation of genes involved in cell death, DNA and oxidative damage, as shown in Table 3.

TABLE 3

| Monocyte/ Macrophage markers | Fold change over NC | Inflammatory markers | Fold change over NC | Acute Phase Reactant Proteins | Fold change over NC |
|---|---|---|---|---|---|
| CD14 | 336 | GAS 6 | 2 | Serum myeloid A1 | -4.6 |
| MARCO | 15 | ICAM 1 | 2 | Serum myeloid A2 | -3.3 |
| CD36 | 4.9 | GADD45 | -6.6 | β2 macroglobulin | 2.6 |
|  |  |  |  | Orosomucoid 2 | 4 |

Mice were then selected for drug treatment based on the criteria set out above, and typically exhibited the characteristics in Table 1, supra.

EXAMPLE 5

Treatment with Compound 2

Following 120-150 days on the HFD, mice in the NASH group were treated with Compound 2 (5 or 10 mg/Kg/day) or vehicle (10% Encapsin) for 42 days. Fasting and post prandial (PP) blood draws were taken at the beginning of the study (compound treatment) to identify and confirm the NASH group and during the study to evaluate various pharmacological responses. Since the NASH mice are severely hyperinsulinemic compared to NC mice, glucose tolerance testing (GTT, measures peripheral insulin resistance) was performed to evaluate the effect of Compound 2 on improvement of peripheral insulin sensitivity. Treatment was administered for 42 days (separate experiments). Body weight and food intake was measured throughout the study.

Oral administration of selective PPAR δ agonist Compound 2 significantly impacted each of the key features of metabolic NASH. Specifically, the mice exhibited (1) reduced levels of serum transaminases AST and ALT; (2) reduced lipid accumulation in the liver (32%, p<0.03 vs. vehicle), (3) attenuated progression to fibrosis measured by histological presence of collagen deposits in the liver, (4)

normalized levels of inflammatory marker TGFβ-1 (p<0.05 vs. vehicle), (5) attenuated macrophage infiltration in the liver, (6) normalized levels of plasma MCP-1 (p<0.05 vs. vehicle), (7) increased weight loss (p<0.05 vs. vehicle), (8) improved glucose disposal, and improved insulin sensitivity (both p<0.05 vs. vehicle).

Treatment with Compound 2 (42 days of 5 mg/kg/day) reduced serum transminase levels in the treated NASH mice demonstrating a 43% reduction each in AST (201±23 vs. 115±19; p<0.02, respectively) and ALT (108±15 vs. 62±13; p<0.05) compared to the vehicle group.

Figure 2B:
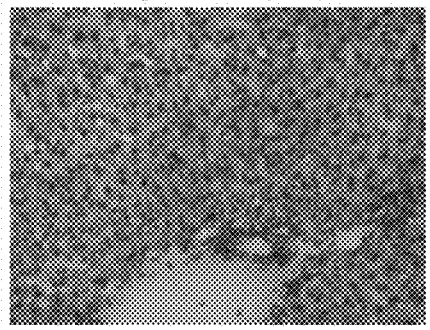
FIG. 2B shows a comparison of LFT and inhibition of hepatic lipid accumulation as seen in histological images from the livers of HFD mice either administered the compound of Example 2 (Compound 2, 42 days of 5 mg/kg/day, bottom image) or vehicle (top image).
Figure 2B:
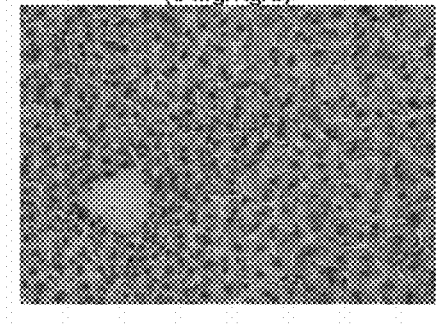
Figure 3A:
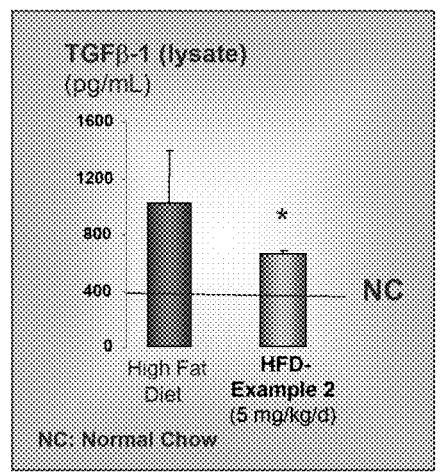
FIG. 3A shows a comparison of TGFβ-1 levels as between HFD mice either administered the compound of Example 2 (Compound 2, 42 days of 5 mg/kg/day), or vehicle. Comparable mean levels of TGF-β1 in NC mice are also shown as a line.

Treatment with Compound 2 (42 days of 10 mg/kg/day) resulted in reduced fat accumulation in the livers of treated vs. non-treated NASH mice as shown in FIG. 2B and Table 4 below, in which reduction in steatosis is evidenced by calculated percent field area occupied by stained oil deposits. Field area for NC mice is also reported.

TABLE 4

| Cell Structure | Percent Field Area NC | Percent Field Area HFD + Vehicle | Percent Field Area HFD + Compound 2, 10 mg/kg |
|---|---|---|---|
| Cytoplasm | 58.9% +/− 9.5 | 91% +/− 2.4 | 38.6% +/− 2.3 |
| Lipid | 1.7% +/− 1.1 | 47.7% +/− 5.5 | 16.0% +/− 7.6 |

Figure 3B:
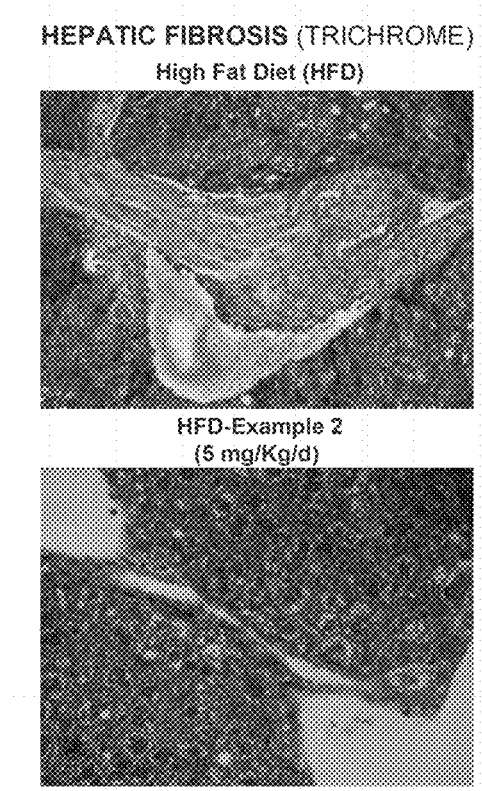
FIG. 3B shows a comparison of hepatic fibrosis as seen in histological images from the livers of HFD mice either administered the compound of Example 2 (Compound 2, 42 days of 2 mg/kg/day, bottom image) or vehicle (top image).

Progression of fibrosis was attenuated by administration of Compound 2 (10 mg/Kg/day), as evidenced by Trichrome staining of liver sections (FIG. 3B, 41%; p<0.03). This was accompanied by parallel decrements TGFβ levels in the liver lysates were (FIG. 3A, 49%; p<0.01 by Student's T test; samples of unequal variance). These results suggest the improvement in NASH-induced fibrosis occurs at least in part via the downregulation of the TGFβ dependent pathway in the liver.

Lending support to the fibrosis histology data, microarray analyses demonstrated that treatment with Compound 2 (35 days, 10 mg/kg/day) compared to the vehicle (10% Encapsin) reduced genes involved in matrix synthesis as well as inhibitors of matrix degradation. mRNA was isolated from the liver of 4 mice collected during sacrifice (4 hours post dosing in the fed state) from the vehicle and the treated groups. Gene expression was analyzed using Affynmatrix microarray followed by GOBY software analyses. Data (Table 5, below) represent average fold change in gene expression in the Compound 2/vehicle group.

TABLE 5

| Fibrosis and matrix promoting genes | Fold change over vehicle |
|---|---|
| Col1a1 | −6.3 |
| Col1a2 | −3 |
| Col3a1 | −3 |
| Col5a2 | −2.2 |
| Col6a2 | −8.9 |
| Vimentin | −2.3 |
| Fibronectin | Not changed |
| Timp 1 | −4.5 |
| Timp 2 | Not changed |
| CTGF | Not changed |

NASH-induced inflammation and lipid accumulation in the liver promotes infiltration of monocytes from peripheral circulation into the liver. Hepatic inflammatory status of NASH mice was assessed by histological assessment of the presence of macrophage specific markers including F4/80 in liver sections. An F4/80 antibody stain used is to quantitatively differentiate monocyte/macrophage cell population in the blood and tissue: infiltrating monocytes are F4/80 bright whereas liver macrophages (Kupffer cells) are F4/80 dull. There was a striking increase in the number of F4/80 bright macrophages in the liver of the NASH mice (data not shown) that is attenuated by treatment with Compound 2 (42 days, 5 mg/Kg/day) treated NASH (FIG. 4).

In parallel, MCP-1 levels were also reduced in plasma (34%; p<0.006) and similar trend was observed in the liver lysates (31%; p=0.08, see FIG. 4A), of treated (Compound 2, 42 days of 5 mg/kg/day) vs. untreated mice, suggesting the treatment with a PPARδ activator may in part interfere with the chemotactic gradient contributing to the macrophage accumulation in the liver.

Treatment of NASH mice with Compound 2 (21 days, 10 mg/Kg/day) improved peripheral insulin resistance as demonstrated by improved glucose clearance and reduced insulin secretion during intraperitoneal glucose tolerance testing (ipGTT) compared to vehicle-treated animals. Simultaneous lowering of both glucose and insulin AUCs during GTT suggests an overall improvement of NASH-induced peripheral insulin resistance by activation of PPARδ.

Changes in expression of genes involved in cell death, DNA and oxidative damage in the liver of treated (10 mg/kg/day, 35 days) group compared to the vehicle (10% Encapsin) group were also seen, suggesting that treatment with PPARδ activators such as Compound 2 can attenuate cell death, inflammation, and oxidative damage in the NASH liver. mRNA was isolated from the liver of 4 mice collected during sacrifice (4 hours post dosing in the fed state) from the vehicle and the compound treated groups. Gene expression was analyzed using Affynmatrix microarray followed by GOBY software analyses. Data (Table 6, below) represent average fold change in gene expression in the Compound 2/vehicle group. Microarray analyses (Table #) demonstrated reduction in monocyte/macrophage specific markers (CD 14 and MARCO) as well as inflammatory markers (ICAM-1 and S100 A6) and acute phase reactant proteins (Serum amyloid A1 and A2 and Orosomucoid 2). In contrast, GADD45, a gene known to have anti-inflammatory activities and protective function against DNA damage, was upregulated in the treated group.

TABLE 6

| Monocyte/ Macrophage markers | Fold change over vehicle | Inflammatory markers | Fold change over vehicle | Acute Phase Reactant Proteins | Fold change over vehicle |
|---|---|---|---|---|---|
| CD14 | −2 | GAS 6 | not changed | Serum myeloid A1 | −1.9 |
| MARCO | −2.5 | ICAM 1 | −2.1 | Serum myeloid A2 | −2.2 |
| CD36 | not changed | GADD45 | 8 | β2 macroglobulin | not changed |
| | | | | Orosomucoid 2 | −2.4 |

The data, in toto, shows selective activation of PPARδ can treat NASH, a major cause of cirrhosis.

Blood Collection

Tail blood was collected into EDTA capillary tubes (Becton, Dickinson and Company, Franklin Lakes, N.J., Cat #365973). Upon sacrifice, blood was collected by cardiac puncture using a 1 mL Syringe Tuberculin Slip Tip (Becton, Dickinson & Company, Cat #309602) and B-D25G 5/8 needle (Becton Dickinson, Franklin Lakes, N.J., Cat #305122) and saved into Microtainer brand tube with EDTA (Becton, Dickinson and Company, Cat #365973). The blood was spun for 8 minutes at 8500 rpm at 4° C. (Eppendorf, Centrifuge 5415R, New York, N.Y.). Plasma was collected and stored at −20° C. for further analyses Clinical Chemistry Panel 80 μL EDTA plasma was diluted with 80 μL Dulbecco's phosphate buffered saline (Gibco, Grand Island, N.Y., Cat #14040-133) and analyzed in Olympus AU600 (Olympus, London, UK) for the following endpoints. The lower and upper limit ranges were according to the assay values provided by the JAS Diagnostics, INC (Miami, Fla.).
  Glucose (LL 94-116, UL 297-353 mg/dL, Cat # JAS GLU2-125)
  Triglycerides (LL 46-102, UL 128-168 mg/dL, Cat # TRI2-125)
  ALT/GPT (LL 10-34, UL 64-114 U/L, Cat # JAS ALT2-125)
  AST/GOT (LL 18-46, UL 121-187 U/L, Cat # JAS AST2-125)
  Multi-Chemistry calibrator (Albumin: 3.9 g/dL, Cholesterol: 212 mg/dL,
  Creatinine: 4.4 mg/dL, Glucose: 220 mg/dL, Triglycerides: 116 mg/dL, Cat # JAS CAL1-5)
  Multi-Chemistry control level 1 (Range: See above for each constituent, Cat # JAS CON1-5)
  Multi-Chemistry control level 2 (Range: See above for each constituent, Cat # JAS CON2-5)

All of the reagents used in analyzing the clinical panel were obtained from Alternative Biomedical Solutions (Irving, Tex.). Note that each LL (lower limit), UL (upper limit) and set point values differ depending on the kit lot number. The values here are of: Multi-Chemistry calibrator (Kit lot # E091012K), HDL/LDL cholesterol calibrator (Kit lot # F081031B), Multi-Chemistry control level 1 (Kit lot # E052011K), Multi-Chemistry control level 2 (Kit lot # E05311K), HDL/LDL cholesterol control (Kit lot # F024021K).

Glucose Tolerance Testing (GTT)

Mice were then fasted overnight at 1700 hours for an experiment the following morning at 9:30 am. The animals were restrained in a towel to reduce handling stress and blood collection was from tail nick. Heat lamps were turned on 5 minutes prior to blood draws to warm animals slightly facilitating the flow of blood resulting in a decreased collection time. Blood glucose was measured using an Accu-check Compact Monitoring Kit (Roche Diagnostics, Indianapolis, Ind., Cat #3149137). Blood was also collected (~100 μl) into EDTA microvettes (Sarstedt, Newton, N.C., Cat#16.444.100) for insulin ELISA analysis. After baseline blood collection, 2 g/kg Dextrose (Hospira, Lake Forest, Ill., NDC#0409-6648-02) was administered by intraperitoneal injection followed by glucose readings and blood draws (~50 ul) at time points of 15, 30, 60, and 120 minutes post glucose challenge. Mice were kept in their home cages in between collection intervals.

Immunoassays

Insulin fasting plasma samples were tested using Mercodia ultra sensitive mouse insulin ELISA: 2.5 μL EDTA plasma, ALPCO Diagnostics, Uppsala, Sweden, Cat #08-10-1150-99, LOQ (0.22-7.1 μg/L). Mouse JE/MCP-1 post prandial samples were collected at sacrifice. 12.5 μL EDTA plasma, R & D Systems, Minneapolis, Minn., Cat # MFE00, LOQ (15.6-1000 pg/mL).

Necropsy and Sample Collection

Animals were placed in Surgivet/ANESCO ISOTECY chamber (Vetequip Incorporated, Waukesha, Wis.) filled with Isoflurane (1-chloro-2,2,2-trifluoroethyl difluoromethyl ether, CAS#26675-46-7), USP Liquid for Inhalation (Baxter, Deerfield, Ill., Cat #10019-360-40) for anesthetization. Cardiac blood is taken with BD 1 mL Syringe Tuberculin Slip Tip (Becton, Dickinson & Company, Franklin Lakes, N.J., Cat #309602) with B-D25G 5/8 needle (Becton Dickinson, Franklin Lakes, N.J., Cat #305122) and was saved into Microtainer brand tube with EDTA (Becton, Dickinson and Company, Cat #365973). The heart, liver, kidney, adipose (white and brown) and muscle were collected using fine forceps and fine scissors. Tissues were stored in aluminum foils and flash frozen in liquid nitrogen for further analyses. ~100 mg of heart, liver, adipose (white) were saved in tubes containing 1 mL RNAlater RNA Stabilization Reagent (Qiagen, Valencia, Calif., Cat #76106) and flash frozen in liquid nitrogen for gene array analyses. The liver, muscle and adipose (white) were fixed in 10% Zinc Formalin (Fisher Diagnostics, Middletown, Va., Cat#032-065, CAS #50-00-0) for histology analyses. In addition, the liver and muscle were frozen in Cryomold Standard Disposable Specimen Mold 25 mm×20 mm×5 mm (Sakura Finetechnical U.S.A., Inc., Torrance, Calif., Cat #4557) with O.C.T Compound (Sakura Finetechnical U.S.A., Inc., Torrance, Calif., Cat #4583) and frozen on dry ice mixed with 2-Methylbutane (Isopentane) (Sigma-Aldrich, St. Louis, Mo., CAS #78-78-4, Cat #270342-2L).

Staining Procedures

Staining was prepared with Oil Red 'O' that stains fat deposits red on frozen tissues where positive staining indicates lipid accumulation. Trichrome staining was used to illuminate fibrosis; collagen deposits appear blue and positive staining indicates fibrosis.

F4/80 Staining Procedure

F4/80 stain was used to illustrate macrophage infiltration in liver tissue. The following protocol was followed:
  1. Check the number of sections per slide; if there is 1 section then use 2 slides from the same group per staining run (1 for ctrl IgG and 1 for primary antibody of interest). If there are 2 sections per slide then use 1 slide per group per run and separate the sections using a PAP pen.
  2. De-paraffin slides through 3×5-minutes Propar clearant, and re-hydrate with 5-minutes each in decreased concentrations of reagent alcohol to water (100%, 95%, 75%, water).
  3. Use Citrate buffer pH 6.0 for HIER (heat-induced epitope retrieval). Pre-heat buffer in plastic container for 2+ minutes to boiling, place slides carefully in the liquid, cover, and heat slides at 20% power for 10 minutes. Put entire container on ice to cool for 20 minutes. Rinse 1× in PBS.
  4. Block with CAS block with 10% added goat serum for 30 minutes.

5. Aspirate block and directly apply rat anti-mouse F4/80 or ctrl rat IgG$_{2A}$ at 1:100 (10 ug/ml) in PBS. Incubate for 1 hr. Rinse in 3×5-minutes PBS.
6. Apply goat anti-rat FITC-conjugated secondary antibody at 1:100 in 10% goat serum in PBS. Incubate for 30 minutes. Rinse 3×5-minutes in PBS.
7. Apply Slow-fade mounting medium with DAPI nuclear counterstain and apply glass cover slip.
8. Visualize on the Zeiss scope using FITC and DAPI filter cubes. Expose FITC signal for approximately 0.5-1.0 s using objectives 20× and 40×. Expose DAPI signal for approximately 0.05-0.08 s at 20× and 40× objective use.

Microarray Analyses

Total RNA was extracted using the RNeasy mini protocol (Qiagen, Cat: 74106), gene array analyses was performed using Mouse Genome 430.2.0 Affymetrix CHIP and VAMPIRE analyses software at the Veterans Affair, UCSD core facility, UCSD, San Diego, Calif.

Reagents Used

The following list includes reagents used in assays above. It is not intended to be comprehensive or exclusive. Those of skill in the art will supplement or modify it as necessary.
Reagent Staining Rack (Tissue Tek, VWR Scientific, Pittsburgh, Pa., cat. #25608-902)
Propar Clearant (Anatech Ltd, Battle Creek, Mich., cat. #511)
Reagent Alcohol (Fisher Scientific, Pittsburgh, Pa., cat. #HC-600-1GAL)
Citrate buffer pH 6.0 (Zymed/Invitrogen, Carlsbad, Calif., cat. #00-5000)
CAS block (Zymed/Invitrogen cat. #00-8120)
goat serum (Caltag/Invitrogen, Cat. #10000-C)
rat anti-mouse F4/80 (Abcam, Cambridge, Mass., cat. #6640)
ctrl rat IgG$_{2A}$ (Abcam cat. #18536)
goat anti-rat FITC-conjugated secondary antibody (Zymed/Invitrogen cat. #81-9511)
Slow-fade mounting medium with DAPI (Molecular Probes/Invitrogen cat. # S-8120)

All references cited herein are incorporated by reference in their entireties. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of NASH comprising administering to a subject in need thereof a therapeutically effective amount of a compound selected from the group consisting of (S)-4-[cis-2,6-dimethyl-4-(4-trifluoromethoxy-phenyl)-piperazine-1-sulfonyl]-indan-2-carboxylic acid tosylate and (S)-4-[cis-2,6-dimethyl-4-(4-trifluoromethoxy-benzyl)-piperazine-1-sulfonyl]-indan-2-carboxylic acid tosylate, or a salt thereof.

2. The method as recited in claim 1, wherein said compound is (S)-4-[cis-2,6-dimethyl-4-(4-trifluoromethoxy-benzyl)-piperazine-1-sulfonyl]-indan-2-carboxylic acid tosylate, or a salt thereof.

* * * * *